(12) United States Patent
Gozlan et al.

(10) Patent No.: US 10,537,103 B2
(45) Date of Patent: Jan. 21, 2020

(54) ANTIBACTERIAL COMPOSITION CONTAINING AN ISOMER MIXTURE OF MONOSACCHARIDE ALKYL MONOACETALS OR MONOETHERS

(71) Applicants: TEREOS STARCH & SWEETENERS BELGIUM, Aalst (BE); UNIVERSITÉ CLAUDE BERNARD LYON 1, Villeurbanne (FR); CENTRE NATIONAL DE LA RECHERCHE SCIENTIFIQUE (C.N.R.S.), Paris (FR)

(72) Inventors: Charlotte Gozlan, Villeurbanne (FR); Dorine Belmessieri, Villeurbanne (FR); Marie-Christine Duclos, Villeurbanne (FR); Nicolas Duguet, Villeurbanne (FR); Marc Lemaire, Villeurbanne (FR); Gérard Lina, Villeurbanne (FR); Oana Dumitrescu, Villeurbanne (FR); Andreas Redl, Aalst (BE)

(73) Assignees: TEREOS STARCH & SWEETENERS BELGIUM, Aalst (BE); UNIVERSITÉ CLAUDE BERNARD LYON 1, Villeurbanne (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 40 days.

(21) Appl. No.: 15/537,869

(22) PCT Filed: Dec. 17, 2015

(86) PCT No.: PCT/IB2015/059731
§ 371 (c)(1),
(2) Date: Jun. 19, 2017

(87) PCT Pub. No.: WO2016/098046
PCT Pub. Date: Jun. 23, 2016

(65) Prior Publication Data
US 2017/0347653 A1    Dec. 7, 2017

(30) Foreign Application Priority Data
Dec. 17, 2014 (FR) .................. 14 02895

(51) Int. Cl.
| | | |
|---|---|---|
| *A61K 31/7028* | (2006.01) | |
| *C07H 15/04* | (2006.01) | |
| *A61K 31/7004* | (2006.01) | |
| *A61P 31/04* | (2006.01) | |
| *A01N 43/90* | (2006.01) | |
| *A01N 43/08* | (2006.01) | |
| *A61K 31/341* | (2006.01) | |
| *C07D 307/20* | (2006.01) | |
| *A01N 43/16* | (2006.01) | |

(52) U.S. Cl.
CPC ............. *A01N 43/90* (2013.01); *A01N 43/08* (2013.01); *A01N 43/16* (2013.01); *A61K 31/341* (2013.01); *A61K 31/7004* (2013.01); *A61K 31/7028* (2013.01); *A61P 31/04* (2018.01); *C07D 307/20* (2013.01); *C07H 15/04* (2013.01)

(58) Field of Classification Search
None
See application file for complete search history.

(56) References Cited

U.S. PATENT DOCUMENTS

| | | | | |
|---|---|---|---|---|
| 2,974,134 A | * | 3/1961 | Pollitzer | C07H 15/04 536/120 |
| 5,576,425 A | | 11/1996 | Hill | |
| 5,618,840 A | * | 4/1997 | Wright | A61K 9/1272 514/549 |
| 5,728,372 A | * | 3/1998 | Pinzon | A61K 8/29 424/400 |
| 9,499,559 B2 | * | 11/2016 | Gozlan | C07D 493/04 |
| 10,221,148 B2 | * | 3/2019 | Gozlan | B01F 17/0021 |
| 2017/0121298 A1 | * | 5/2017 | Gozlan | B01F 17/0021 |
| 2018/0000077 A1 | * | 1/2018 | Gozlan | A23L 3/3463 |

FOREIGN PATENT DOCUMENTS

| | | | | |
|---|---|---|---|---|
| EP | c07d | * | 10/1980 | ........... C07D 325/00 |
| JP | 2012-140370 | * | 7/2012 | ............... A61K 8/60 |
| WO | WO2012/148530 A1 | | 11/2012 | |
| WO | WO2014/199345 A1 | | 12/2014 | |
| WO | WO2015/189796 A1 | | 12/2015 | |

OTHER PUBLICATIONS

English machine translation of JP2012-140370 above, downloaded from translationportal.epo.org (Year: 2012).*
U.S. Appl. No. 16/063,679, filed Jun. 2018, Gozlan; Charlotte.*
Zhang et al., "TMDS as a Dual-Purpose Reductant in the Regioselective Ring Cleavage of Hexopyranosyl Acetals to Ethers" European Journal of Organic Chemistry (2012) pp. 1960-1966 (Year: 2012).*
Smith et al., "Synthesis and antimicrobial evaluation of carbohydrate and polyhydroxylated non-carbohydrate fatty acid ester and ether derivatives" Carbohydrate Research vol. 343 pp. 2557-2566 (Year: 2008).*
Nobmann et al., "The antimicrobial efficacy and structure activity relationship of novel carbohydrate fatty acid derivatives against *Listeria* spp. and food spoilage microorganisms" Internationa Journal of Food Microbiology vol. 128 pp. 440-445 (Year: 2009).*

(Continued)

*Primary Examiner* — Eric Olson
(74) *Attorney, Agent, or Firm* — Symbus Law Group, LLC; Clifford D. Hyra

(57) ABSTRACT

A bactericidal or bacteriostatic composition comprising an isomer mixture of monosaccharide alkyl monoethers or monoacetals, its use in the treatment or prevention of Gram-positive bacterial infections, its use as a hygiene or dermatological product for external use and a method for disinfecting surfaces.

20 Claims, No Drawings

(56) References Cited

OTHER PUBLICATIONS

Matsumura et al., "Surface Activities, Biodegradability and Antimicrobial Properties of n-Alkyl Glucosides, Mannosides and Galactosides" JAOCS vol. 67 No. 12 pp. 996-1001 (Year: 1990).*
Written Opinion and International Search Report dated Feb. 24, 2016.
Shuichi Matsumura et al: Surface activities, biodegradability and antimicrobial properties of n-alkyl glucosides, mannosides and galactosides11 , Journal of the American Oil Chemists' Society, vol. 67, No. 12, Dec. 1, 1990 (Dec. 1, 1990), pp. 996-1001, XP055029089,ISSN: 0003-021X, DOI: 10.1007/BF02541865 tablespage 1000.
Smith A et al: Synthesi s and antimicrobial evaluation of carbohydrate and polyhydroxylated non-carbohydrate fatty acid ester and ether derivatives11 , Carbohydrate Research, Pergamon, GB, vol. 343, No. 15, Oct. 13, 2008 (Oct. 13, 2008), pp. 2557-2566, XP025408848.

* cited by examiner

ANTIBACTERIAL COMPOSITION CONTAINING AN ISOMER MIXTURE OF MONOSACCHARIDE ALKYL MONOACETALS OR MONOETHERS

This application claims the benefit of French patent application Ser. No. 14/02,895, filed Dec. 17, 2014, which is hereby incorporated by reference in its entirety.

TECHNICAL DOMAIN

Embodiments of the present invention relate to a bactericidal or bacteriostatic composition comprising a positional isomer mixture of alkyl monosaccharide monoethers or monoacetals, its use in the treatment or prevention of Gram-positive bacterial infections, its use as a hygiene or dermatological product for external use and a method for disinfecting surfaces.

TECHNICAL BACKGROUND

Antimicrobial compounds are defined as molecules that can inhibit or stop the growth of micro-organisms or kill them. In this context, they are commonly used to prevent or treat human and animal infections, and in the agrifood industry to prevent multiplication of pathogenic bacteria in food. Widespread use of antimicrobial compounds favors the emergence of resistant infectious agents. The spread of bacteria that has acquired resistance mechanisms for the most widely used antimicrobial compounds is a more and more alarming major public health problem (J. S. Bradley et al. Lancet Infect. Dis. 2007; 7:68-78).

As an illustration, many strains resistant to antibiotics for the most pathogenic species of genus *Staphylococcus*, i.e. *Staphylococcus aureus*, have been isolated. *Staphylococcus* infections represent a high percentage of serious infections. What is more, almost half of nosocomial infections are reportedly related to *staphylococcus*. Mention may be made of the many strains of *Enterococcus faecalis* or *Enterococcus faecium* that are resistant to commonly used antibiotics. Although they are less virulent than staphylococci in particular, an increasing number of multiresistant *enterococcus* strains and more recently epidemics of enterococci resistant to glycopeptides, the antibiotics of recourse for this bacterial family, have been identified.

Another antibioresistance phenomenon has been described that might not only be related to the excessive use of antibiotics, but to food storage methods. So for example it has been shown that *Listeria monocytogenes* is more resistant to antibiotics after having undergone osmotic stress, at a low temperature or in an acidic medium (Anas A. et al. (2015) Food Microbiology, Volume 46, April, Pages 154-160). That is, the human contamination comes from food. In addition, although it is relatively rare, human listeriosis is a serious infection with mortality estimated at 50%. Accordingly, the emergence of antibiotic resistance in *L. monocytogenes* that could be caused by modern storage or treatment methods for food constitutes a serious threat to public health.

Although several mechanisms are often involved simultaneously in antibiotic resistance, it is common to classify it into three categories: (a) lack of antibiotic penetration into the bacterium, (b) inactivation or excretion of the antibiotic by bacterial enzymatic systems and (c) lack of affinity between the bacterial target and the antibiotic. These three resistance mechanism categories have a structural component, i.e. the mechanisms used are dependent on the structure of the molecule concerned.

No process in the prior art can produce an isomeric mixture of biosourced compounds with low toxicity and low cost.

Nevertheless, biosourced compounds have been described. Accordingly, different compounds used as antimicrobials have been described, among which are fatty acids and their corresponding polyhydroxylated esters that are active against Gram-positive bacteria and having long aliphatic chains. As an indication, one of the most active antimicrobials is monolaurine, a glycerol monoester with a C12 aliphatic chain. Its trade name is LAURICIDIN®. This compound is used as a food additive to inhibit bacterial growth (E. Freese, C. W. Sheu, E. Galliers. Nature 1973, 241, 321-325; E. G. A. Verhaegh, D. L. Marshall, D.-H. Oh. Int. J. Food Microbiol. 1996, 29, 403-410). The ester function of the monolaurine is sensitive to esterases, so this compound degrades quickly and has a short half-life.

Also described are antimicrobials derived from sugar considered as particularly attractive because of their biodegradability, their low toxicity and environmental impact.

Examples of antimicrobials derived from sugar are the esters derived from sugar that are also used industrially for antimicrobial applications because their raw materials and production costs remain relatively low. Mention may be made for example of sorbitan caprylate described in international patent application WO2014/025413 in mixture with Hinokitiol in an antimicrobial formulation. According to this application, this formulation will inhibit or kill Gram-positive and negative bacteria, fungi and/or yeast.

Also described is the use of disaccharide esters as antimicrobial agents in the food industry. Dodecanoyl sucrose is one of the most used. It is reportedly particularly active against *L. monocytogenes* (M. Ferrer, J. Soliveri, F. J. Plou, N. López-Cortés, D. Reyes-Duarte, M. Christensen, J. L. Copa-Patiño, A. Ballesteros, Enz. Microb. Tech., 2005, 36, 391-398). Nevertheless, it is also described as weakly inhibiting the growth of *S. aureus*, for hospital applications (J. D. Monk, L. R. Beuchat, A. K. Hathcox, J. Appl. Microbiol., 1996, 81, 7-18). It reports that the sucrose ester presents properties that are bacteriostatic (stops bacterial growth) but not bactericidal (kills the bacteria).

In addition, the synthesis of sugar esters presents many drawbacks. First, in spite of the low production cost, synthesizing esters, more particularly for di- and trisaccharides, is problematic because of sugars' high functionality, which causes the formation of a mixture of mono-, di- and polyesters and the presence of a polar solvent, such as dimethylformamide (DMF) and pyridine, is generally necessary to better solubilize the highly polar reagents. However, these solvents are classed as carcinogenic, mutagenic and reprotoxic (CMR) and their use must be avoided. To solve this problem, enzymatic synthesis was used but the need to use very dilute media in these conditions makes production limited.

Moreover, the ester functions on these compounds are easy for the esterases present in the cells to hydrolyze. The molecules released after this hydrolysis, i.e. the sugar and the fatty acid, have little or no antimicrobial properties (the fatty acid is slightly active). This causes instability that is responsible for reduced activity in these compounds.

SUMMARY

To produce an antibiotic composition having lower chances of allowing resistance to develop, a composition may be used containing a mixture of compounds having antibiotic activity but including structural differences that can reduce the chances of developing bacterial resistance, in particular, a composition comprising an isomeric mixture of compounds having antibiotic activity.

A new antibiotic composition has low toxicity and low environmental impact. A biodegradable composition that can be obtained in large quantities from renewable resources, at low cost to be perfectly accessible for industrial application but also as effective as non-biosourced antimicrobials.

To obtain an antibiotic composition unfavorable to the development of resistance comprising effective and stable antimicrobial agents, embodiments of the invention propose a positional isomer mixture of alkyl monosaccharide monoethers or monoacetals obtained in conditions that are not costly while respecting the environment and not representing a hazard for topical applications or by ingestion.

DETAILED DESCRIPTION OF EMBODIMENTS

Bactericidal or Bacteriostatic Composition

Embodiments of the invention relate to a bactericidal or bacteriostatic composition comprising a mixture of alkyl monoether or monoacetal positional isomers of monosaccharides or monosaccharide derivatives, said monosaccharide derivative being a glycosylated and/or hydrogenated and/or dehydrated monosaccharide, said mixture of monoether or monoacetal positional isomers of alkyl monosaccharide or monosaccharide derivative being obtained by a process comprising the following steps:
 a) an acetalization or trans-acetalization of a monosaccharide or monosaccharide derivative by an aliphatic aldehyde containing from 11 to 18 carbon atoms or the acetal thereof
 b) optionally, catalytic hydrogenolysis of the monosaccharide alkyl acetal or monosaccharide derivative obtained in a) preferentially, without an acid catalyst, and
 c) recovery of a mixture of monosaccharide or monosaccharide derivative alkyl monoether positional isomers obtained in b) in which the alkyl group (R) comprises between 11 to 18 carbon atoms
  or
  recovery of a mixture of monosaccharide or monosaccharide derivative alkyl monoacetal positional isomers obtained in a) in which the alkyl group (R) comprises between 11 to 18 carbon atoms.

Embodiments of the invention relate to a bactericidal or bacteriostatic composition comprising a mixture of alkyl monoether or monoacetal positional isomers of monosaccharides or monosaccharide derivatives, said monosaccharide derivative being a glycosylated and/or hydrogenated and/or dehydrated monosaccharide, said mixture of monoether or monoacetal positional isomers of alkyl monosaccharide or monosaccharide derivative being obtained by a process comprising the following steps:
 a) optionally, a dehydration of a monosaccharide or a monosaccharide derivative to obtain a monoanhydrosaccharide;
 b) an acetalization or trans-acetalization of the monosaccharide or monoanhydrosaccharide or monosaccharide derivative obtained in a) by,
  i. an aliphatic aldehyde containing from 11 to 18 carbon atoms, by acetalization, or
  ii. an aliphatic aldehyde acetal containing from 11 to 18 carbon atoms, by trans-acetalization;
 c) optionally, catalytic hydrogenolysis of the monosaccharide alkyl acetal or monosaccharide derivative obtained in b) preferentially, without an acid catalyst, and
 d) recovery of a mixture of monosaccharide or monosaccharide derivative alkyl monoether positional isomers obtained in c) in which the alkyl group (R) comprises between 11 to 18 carbon atoms
  or
  recovery of a mixture of monosaccharide or monosaccharide derivative alkyl monoacetal positional isomers obtained in b) in which the alkyl group (R) comprises between 11 to 18 carbon atoms.

As used here, the term "monosaccharide" refers to polyhydroxyaldehyde (aldose) or polyhydroxyketone (ketose).

Preferably, said monosaccharide unit has 6 carbon atoms, also called "hexose." The term "hexose" refers to aldohexoses, ketohexoses and to their derivatives and analogs.

Preferably, said hexose is chosen from the group formed by glucose, mannose, galactose, allose, altrose, gulose, idose and talose.

According to one embodiment, the monosaccharide derivative is an anhydrosaccharide or a sugar-alcohol.

An "anhydrosaccharide" is a monosaccharide obtained by dehydration, by the elimination of one or more molecules of water from a corresponding mono-, di-, tri- or oligosaccharide or a mono-, di-, tri- or oligosaccharide derivative such as a hydrogenated mono-, di-, tri- or oligosaccharide. An example of a suitable anhydrosaccharide may be a monoanhydrosaccharide such as a hexitan chosen from the group formed by 1,4-anhydro-D-sorbitol (1,4-arlitan or sorbitan); 1,5-anhydro-D-sorbitol (polygalitol); 3,6-anhydro-D-sorbitol (3,6-sorbitan); 1,4(3,6)-anhydro-D-mannitol (mannitan); 1,5-anhydro-D-mannitol (styracitol); 3,6-anhydro-D-galactitol; 1,5-anhydro-D-galactitol; 1,5-anhydro-D-talitol and 2,5-anhydro-L-iditol.

The preferred hexitan is a derivative from the dehydration of sorbitol to form for example, 1,4-sorbitan, 3,6-sorbitan or 2,5-sorbitan.

According to one embodiment, said monosaccharide derivative is a sugar-alcohol. As it is used here, the term "sugar-alcohol," also known as the name "polyol" refers to a hydrogenated form of monosaccharide whose carbonyl group (aldehyde or ketone) has been reduced to a primary or secondary hydroxyl. Said sugar-alcohol may be, for example, chosen from the group formed by erythritol, threitol, arabitol, ribitol, mannitol, sorbitol, galactitol, volemitol, isomalt, maltitol, lactitol, maltotriitol, maltotetraitol and polyglycitol. Preferably, the sugar-alcohol is a hexitol chosen for example from mannitol, sorbitol, galactitol and volemitol, more preferentially, sorbitol, xylitol or mannitol.

According to one embodiment, the process according to embodiments of the invention may comprise a step of dehydrating said monosaccharide to obtain a monoanhydrosaccharide for example, when the monosaccharide derivative is a sugar-alcohol. Typically, the monosaccharide is melted before the dehydration step. The dehydration step may be conducted with a catalyst, for example, with an acid catalyst.

The dehydration step may be conducted under a hydrogen atmosphere at a pressure preferably of about 20 to 50 bar.

The dehydration step may be conducted at a temperature comprised between 120 and 170° C., preferably between 130 and 140° C.

Typically, the monosaccharide derivative is purified after the dehydration step, for example by crystallization, recrystallization or chromatography.

According to one embodiment, said monosaccharide derivative is a glycosyl monosaccharide otherwise called an alkylglycoside.

As used here, the term "alkylglycoside" refers to a monosaccharide where the reducing portion is connected by bond to an alkyl group by glycosylation, as described in the state of the art. Typically, the monosaccharide may be related to the alkyl group by an oxygen atom (an O-glycoside), a nitrogen atom (a glycosylamine), a sulfur atom (a thioglycoside), or a carbon atom (a C-glycoside). The alkyl group may have a varied chain length: preferably, the alkyl group is a C1-C4 alkyl group. An even more preferred alkyl group is a methyl or ethyl group. Typically, the alkylglycoside is a hexoside. Alkyl glycosides may for example be chosen from a group formed of methyl glucoside, ethyl glucoside, propyl glucoside, butyl glucoside, methyl xyloside, ethyl xyloside, propyl xyloside, butyl xyloside, methyl mannoside, ethyl mannoside, propyl mannoside, butyl mannoside, methyl galactoside, ethyl galactoside, propyl galactoside and butyl galactoside.

According to embodiments of the invention, the acetalization or trans-acetalization step comprises:

i) optionally, a step of preheating said monosaccharide or said mixture of monosaccharides, preferably at a temperature comprised between 70 and 130° C., typically between 90 and 110° C., ii) a step of adding the aliphatic aldehyde or an aliphatic aldehyde derivative to said monosaccharide and iii) a step of adding a catalyst preferably an acidic catalyst.

Typically, the aliphatic aldehyde acetal may be a di-alkyl acetal of the corresponding aldehyde. Di-methyl acetals and di-ethyl acetals are preferred.

Step i) is particularly advantageous in that it may be implemented in the absence of solvent.

Preferably, the acid catalyst used during the acetalization or trans-acetalization step and if need be the dehydration step may be a homogeneous or heterogeneous acid catalyst. The term "homogeneous", as used in the expression "homogeneous acid catalyst" refers to a catalyst that is in the same phase (solid, liquid or gas) or in the same aggregate state as the reagent. Conversely, the term "heterogeneous," as used in the expression "heterogeneous acid catalyst" refers to a catalyst that is in a different phase (solid, liquid or gas) as the reagent.

Said acid catalyst used during the acetalization or trans-acetalization step and if need be during the dehydration step may be independently chosen from solid or liquid, organic or inorganic acids, solid acids being preferred. Specifically, the preferred acid catalyst is chosen from para-toluene sulfonic acid, methane sulfonic acid, camphorsulfonic acid (CSA) and sulfonic resins.

Typically, the acetalization or trans-acetalization step is conducted at temperatures comprised between 70 and 130° C., typically between 70 and 90° C. The temperature of the reaction mixtures may vary as a function of the reagents and solvents used. The reaction time is determined by the degree of conversion reached.

According to one embodiment, the acetalization or trans-acetalization step may be conducted by an aliphatic aldehyde or the acetal thereof, typically, a linear or branched aliphatic aldehyde or the acetal thereof. The acetalization or trans-acetalization step may be typically conducted with an aliphatic aldehyde or the acetal thereof having 11, 12, 13, 14, 15, 16, 17 or 18 carbon atoms, for example chosen from undecanal, dodecanal, tridecanal, tetradecanal, pentadecanal, hexadecanal, heptadecanal, octodecanal. Preferably, the C11-C13 aliphatic aldehyde or the acetal thereof is a C12 aliphatic aldehyde or the acetal thereof, for example, a dodecanal or the acetal thereof.

The expression "the acetal thereof" or "their acetal(s)," as used herein covers the di-alkyl acetal of the corresponding C11-C18 aliphatic aldehyde. More particularly, the di-methyl or di-ethyl acetals of the C11-C18 aliphatic aldehyde are preferred.

According to one embodiment, the acetalization or transacetalization step may be conducted with or without solvent. When the reaction is conducted in the presence of a solvent, the solvent is preferably a polar solvent.

Typically, the solvent may be chosen from dimethylformamide (DMF), dimethylsulfoxide (DMSO), dimethylacetamide (DMA), acetonitrile ($CH_3CN$), tetrahydrofuran (THF), 2-methyltetrahydrofuran (2Me-THF), cyclopentyl methyl ether (CPME), methanol (MeOH), ethanol (EtOH), propanol (PrOH), isopropanol (iPrOH), butanol (BuOH), dibutyl ether (DBE), methyl tert-butyl ether (MTBE) and trimethoxypropane (TMP).

In depth experimental work led to a selection of conditions that allow observation of conversion rates and optimal yields during acetalization or trans-acetalization steps. Better results were obtained when the molar ratio [(C11-C18 aliphatic aldehyde or their acetal):monosaccharide] is between 5:1 and 1:5, preferably between 4:1 and 1:4, and advantageously between 3:1 and 1:3.

The inventors have more particularly shown that during an acetalization reaction, the molar ratio of C11-C18 aliphatic aldehyde:monosaccharide comprised between 1:1 and 1:5, preferably between 1:1 and 1:4, and in a preferred manner between 1:3 and 1:2, improves the yields and conversion rates.

The inventors have additionally shown that during transacetalization reactions, a molar ratio of C11-C18 aliphatic aldehyde:monosaccharide comprised between 1:1 and 5:1, preferably between 5:4 and 4:1, and preferably between 3:1 and 4:3, preferably between 3:2 and 2:5, improves the yields and conversion rates. The catalysts used are the same as those of the acetalization reaction.

According to one embodiment, the process of the invention additionally comprises at least one neutralization and/or filtration and/or purification step after any one of the dehydration, if need be, acetalization or trans-acetalization steps.

When a purification step is provided, said purification step may be for example a crystallization, a recrystallization or a chromatography. Preferably, chromatography is conducted using a non-aqueous polar solvent. In general, when a filtration and/or purification step is provided before the hydrogenolysis step, the non-aqueous polar solvent may be the same as that used during the hydrogenolysis step.

Advantageously, the hydrogenolysis step is conducted at a temperature comprised between 80° C. and 140° C., and/or at a hydrogen pressure comprised between 15 and 50 bar, preferably between 20 and 40 bar.

The hydrogenolysis step is conducted advantageously in a polar aprotic solvent, preferably a non-aqueous solvent. In fact, aprotic solvents provide better conversion. Examples of aprotic solvents are, among others, without limitation, alkanes, 1,2,3-trimethoxypropane (TMP), methyl tert-butyl ether (MTBE), tetrahydrofuran (THF), 2-methyl tetrahydrofuran (2Me-THF), dibutyl ether (DBE) and cyclopentylmethylether (CPME). Preferably, the aprotic solvent is CPME. Alkanes are advantageous because they allow better hydrogen solubilization in the medium. However, the conversion is lower than for other aprotic solvents such as CPME. Generally, among alkanes, dodecane and heptane are preferred.

The hydrogenolysis step is conducted preferably in a polar aprotic solvent at a temperature comprised between 80° C. and 140° C., and/or at a hydrogen pressure comprised between 15 and 50 bar, in the presence of a catalyst suitable for hydrogenolysis reactions.

Preferably, the hydrogenolysis step is conducted in a non-aqueous polar solvent at a temperature comprised between 100° C. and 130° C. and/or at a pressure comprised between 25 and 35 bar.

Generally, the hydrogenolysis is conducted in the presence of a suitable catalyst such as a catalyst containing precious metals or common metals. More particularly, the common metals may be iron or non-iron metals. Typically, hydrogenolysis is conducted in the presence of a catalyst containing iron metals.

As an indication, a metal catalyst belonging to the group of iron metals may be nickel, cobalt or iron.

Preferably, hydrogenolysis is conducted using a catalyst containing precious metals such as palladium, rhodium, ruthenium, platinum or iridium.

As a general rule, the catalyst used during hydrogenolysis may be fixed on a substrate such as carbon, alumina, zirconium or silica or any mixture of these. Such a substrate is for example a bead. Accordingly, a palladium catalyst fixed on carbon beads (Pd/C) may be advantageously used. These catalysts may be doped by adding precious metals or common metals. These are called doping agents. Typically, the doping agent represents 1 to 10% by weight of the catalyst.

Embodiments of the invention also relate to a bactericidal or bacteriostatic composition comprising a mixture of positional isomers of alkyl monoethers or monoacetals of the monosaccharide or monosaccharide derivative presenting an ether alkyl or acetal alkyl group on 2 distinct positions of the monosaccharide or monosaccharide derivative and the pharmaceutically acceptable salts thereof in which the alkyl group comprises between 11 to 18 carbon atoms, preferentially from 11 to 13 carbon atoms.

The term "pharmaceutically acceptable salt" denotes any salt that, through administration to the patient, can provide (directly or indirectly) a compound such as that described herein. The preparation of salts may be achieved through processes known in the state of the art.

Preferentially, the monosaccharide is a C6 monosaccharide or derivative thereof, said monosaccharide derivative being a glycosylated and/or hydrogenated and/or dehydrated monosaccharide such as an alkylglycoside; preferentially, the monosaccharide or the monosaccharide derivative is:
 a hexose chosen from the group formed by glucose, mannose, galactose, allose, altrose, gulose, idose and talose.
 a hexitol chosen from mannitol, sorbitol, galactitol and volemitol,
 a hexitan chosen from 1,4-anhydro-D-sorbitol (1,4-arlitan or sorbitan); 1,5-anhydro-D-sorbitol (polygalitol); 3,6-anhydro-D-sorbitol (3,6-sorbitan); 1,4 (3,6)-anhydro-D-mannitol (mannitan); 1,5-anhydro-D-mannitol (styracitol); 3,6-anhydro-D-galactitol; 1,5-anhydro-D-galactitol; 1,5-anhydro-D-talitol and 2,5-anhydro-L-iditol or Typically, the alkylglycoside is a hexoside chosen from glucoside, mannoside, galactoside, alloside, altroside, iodoside and taloside.

"Positional isomer" is understood to mean regioisomers, more particularly understood to mean isomers of alkyl monoethers or monoacetals of monosaccharides or monosaccharide derivatives in which the alkyl monoether or monoacetal group is positioned on different oxygens of the monosaccharide or monosaccharide derivative.

Typically, when the monosaccharide is a hexoside, said alkyl monoacetal group is in the 1,2-O; 2,3-O—; 3,4-O— or 4,6-O— position of the hexoside or when the monosaccharide derivative is a hexitol, said alkyl monoacetal group is in the 1,2-O—; 2,3-O—; 3,4-O—; 4,5-O— or 5,6-O— position of the hexitol or also when the monosaccharide derivative is a hexitan, said alkyl monoacetal group is in the 2,3-O—; 3,5-O— or 5,6-O— position of the hexitan.

Preferentially, when the monosaccharide is a hexoside said alkyl monoether group is in the 2-O—, 3-O—, 4-O— or 6-O— position of the hexoside or when the monosaccharide derivative is a hexitol, said alkyl monoether group is in the 1-O—, 2-O—, 3-O—, 4-O—, 5-O— or 6-O— position of the hexitol or also when the monosaccharide derivative is a hexitan, said alkyl monoether group is in the 2-O—, 3-O—, 5-O— or 6-O— position of the hexitan.

According to a variant, the monosaccharide derivative is a sorbitan and said alkyl mono-acetal group is in the 3,5-O— or 5,6-O— position or said alkyl monoether group is in the 3-O—, 5-O— or 6-O— position.

According to a variant, the monosaccharide derivative is a glucoside and said alkyl mono-acetal group is in the 4,6-O— position or said alkyl monoether group is in the 4-O— or 6-O— position.

Advantageously, the mixture of positional isomers of monosaccharide or monosaccharide derivative alkyl monoethers comprises at least one compound chosen from methyl 4,6-O-pentylidene α-D-glucopyranoside; methyl 4,6-O-hexylidene α-D-glucopyranoside; methyl 4,6-O-octylidene α-D-glucopyranoside, methyl 4,6-O-decylidene α-D-glucopyranoside; methyl 4,6-O-dodecylidene α-D-glucopyranoside; methyl 4,6-O-dodecylidene α-D-glucopyranoside; methyl 4,6-O-dodecylidene α-D-mannopyranoside; methyl 4,6-O-dodecylidene α-D-galactopyranoside and mixtures thereof.

According to one embodiment, the mixture of positional isomers of monosaccharide or monosaccharide derivative alkyl monoacetals comprises at least methyl 6-O-pentyl α-D-glucopyranoside and methyl 4-O-pentyl α-D-glucopyranoside; methyl 6-O-hexyl α-D-glucopyranoside and methyl 4-O-hexyl α-D-glucopyranoside; methyl 6-O-octyl α-D-glucopyranoside and methyl 4-O-octyl α-D-glucopyranoside; methyl 6-O-decyl α-D-glucopyranoside and methyl 4-O-decyl α-D-glucopyranoside, methyl 6-O-dodecyl α-D-glucopyranoside and methyl 4-O-dodecyl α-D-glucopyranoside; methyl 6-O-dodecyl α-D-mannopyranoside and methyl 4-O-dodecyl α-D-mannopyranoside; methyl 6-O-dodecyl α-D-galactopyranoside and methyl 4-O-dodecyl α-D-galactopyranoside or mixtures thereof.

Typically, the composition is bactericidal or bacteriostatic for Gram-positive bacteria.

Advantageously, the bactericidal or bacteriostatic composition is incorporated in a food, cosmetic, pharmaceutical, phytosanitary, veterinary composition or surface treatment composition. Such as for example, a cosmetic and/or dermatological composition for cleansing and/or treating skin, particularly in the form of a cream, a gel, a powder, a lotion, a butter in particular, a shower gel, soap, shampoo, shower bath, deodorant, antiperspirant, moist wipe, sun protection formulation or decorative cosmetic formulation.

Embodiments of the invention also relate to a use of a bactericidal or bacteriostatic composition according to the invention as a hygiene or dermatological product for external use.

Typically a "hygiene product" refers to any product used for cleansing, disinfection or hygiene, including for example a lotion, mousse, spray or liquid but also wipes or any substrate that can be impregnated with the composition according to the invention. The expression "dermatological product" refers to any product intended for application on the skin or mucous membranes.

Use in the Treatment or Prevention of a Gram-Positive Bacterial Infection.

Embodiments of the invention also relate to a composition for use in the treatment or prevention of bacterial infections by Gram-positive bacteria.

"Treatment" is understood to mean curative treatment (aiming to at least reduce, eradicate or stop the development of the infection) in a patient. "Prevention" is understood to mean prophylactic treatment (aiming to reduce the risk of the infection appearing) in a patient.

The "patient" may be, for example, a human being or a non-human mammal (for example a rodent (mouse, rat), a feline, a dog or a primate) affected by or that could be affected by bacterial infections and in particular Gram-positive bacterial infections. Preferably, the subject is a human.

The expression "Gram-positive" refers to bacteria that are colored dark blue or purple by the Gram stain, by contrast with Gram-negative bacteria that cannot retain the purple stain. The staining technique uses bacteria's membrane and wall characteristics.

Typically, the Gram-positive bacteria are bacteria from the phylum of Firmicutes, typically of the class of Bacilli in particular chosen from bacteria of the order of Lactobacillales or Bacillales.

According to one embodiment of the invention, bacteria from the order of Bacillales are chosen from the families Alicyclobacillaceae, Bacillaceae, Caryophanaceae, Listeriaceae, Paenibacillaceae, Pasteuriaceae, Planococcaceae, Sporolactobacillaceae, Staphylococcaceae, Thermoactinomycetacea and Turicibacteraceae.

Typically, bacteria from the Listeriaceae family are for example from the genus *Brochothrix* or *Listeria* and may be typically, chosen from *L. fleischmannii*, *L. grayi*, *L. innocua*, *L. ivanovii*, *L. marthii*, *L. monocytogenes*, *L. rocourtiae*, *L. seeligeri*, *L. weihenstephanensis* and *L. welshimeri*.

When Gram-positive bacteria are bacteria from the Staphylococcaceae family, they are in particular chosen from bacteria from the genus *Staphylococcus*, *Gemella*, *Jeotgalicoccus*, *Macrococcus*, *Salinicoccus* and *Nosocomiicoccus*.

Bacteria from the genus *Staphylococcus* for example chosen from *S. arlettae*, *S. agnetis*, *S. aureus*, *S. auricularis*, *S. capitis*, *S. caprae*, *S. carnosus*, *S. caseolyticus*, *S. chromogenes*, *S. cohnii*, *S. condimenti*, *S. delphini*, *S. devriesei*, *S. epidermidis*, *S equorum*, *S. fells*, *S. fleurettii*, *S. gallinarum*, *S. haemolyticus*, *S. hominis*, *S. hyicus*, *S. intermedius*, *S. kloosii*, *S. leei*, *S. lentus*, *S. lugdunensis*, *S. lutrae*, *S. massiliensis*, *S. micron*, *S. muscae*, *S. nepalensis*, *S. pasteuri*, *S. pettenkoferi*, *S. piscifermentans*, *S. pseudintermedius*, *S. pseudolugdunensis*, *S. pulvereri*, *S. rostri*, *S. saccharolyticus*, *S. saprophyticus*, *S. schleiferi*, *S. sciuri*, *S. simiae*, *S. simulans*, *S. stepanovicii*, *S. succinus*, *S. vitulinus*, *S. warneri* and *S. xylosus*.

According to another embodiment of the invention, bacteria from the order of Lactobacillales are chosen from a family of Aerococcaceae, Carnobacteriaceae, Enterococcaceae, Lactobacillaceae, Leuconostocaceae and Streptococcaceae.

Typically, bacteria from the family of Enterococcaceae are chosen from bacteria from genus *Bavariicoccus*, *Catellicoccus*, *Enterococcus*, *Melissococcus*, *Pilibacter*, *Tetragenococcus*, *Vagococcus*.

Bacteria from genus *Enterococcus* are chosen for example from *E. malodoratus*, *E. avium*, *E. durans*, *E. faecalis*, *E. faecium*, *E. gallinarum*, *E. hirae*, *E. solitarius*, preferentially, *E. avium*, *E. durans*, *E. faecalis* and *E. faecium*.

Bacteria from the genus *Staphylococcus* and more particularly *S. aureus* are responsible for many infections of the skin or mucous membranes such as vaginal or nasal membranes. For example, infections such as folliculitis, abscesses, paronychia, boils, impetigo, infections between the digits, anthrax (staphylococcal anthrax), cellulitis, secondary wound infections, otitis, sinusitis, hidradenitis, infectious mastitis, post-traumatic skin infections or infections on burnt skin.

Bacteria from genus *Enterococcus* and in particular *E. faecalis* are responsible in particular for endocarditis, and infections of the bladder, prostate and epididymis.

Embodiments of the invention also relate to a method for treatment or prevention of a bacterial infection by Gram-positive bacteria, preferentially an infection of the skin or mucous membranes, by administration, preferentially topical, to an individual who needs it, of a therapeutically effective quantity of the composition according to the invention.

In a person infected by a Gram-positive bacterium, "therapeutically effective quantity" is understood to mean sufficient quantity to prevent the infection from changing for the worse, or sufficient to make the infection regress. In a person who is not infected, the "therapeutically effective quantity" is the quantity that is sufficient to protect a person who would come into contact with a Gram-positive bacterium and prevent the occurrence of the infection caused by this Gram-positive bacterium.

Typically, topical administration is done by applying the composition according to the invention to the skin or mucous membranes.

Method for Disinfection or Prevention of Bacterial Colonization of a Substrate

Embodiments of the invention additionally relate to a method for disinfection or prevention of bacterial colonization by Gram-positive bacteria of a substrate comprising putting the substrate into contact with a composition as described.

Typically, the substrate is any substrate that can be colonized by Gram-positive bacteria and that can transmit the infection to an animal by contact or ingestion.

For example, the substrate may be a food of plant or animal origin or a food composition comprising such foods or an extract of these foods and in particular cereals, fruits, vegetables, meat, fish or offal.

The substrate may also be one or more elements selected from among metals, plastics, glass, concrete or stone.

Preferentially the substrate is a utensil, a tool or a device used in the food industry, (cooking utensils, a container, a cold storage system, a refrigerator, cold rooms, etc.) in a hospital environment, such as for example surgical tools or prostheses or for public transit (hand rails, seats, etc.).

Embodiments of the invention also relate to a composition for disinfection, purification, sterilization or purification of surfaces.

Although having distinct meanings, the terms "comprising", "containing", "including" and "consisting of" have been used interchangeably in the description of embodiments, and may be replaced by each other.

The invention will be better understood upon reading the following figures and examples given only as examples.

EXAMPLES

The alkyl sugar acetals (sorbitan and methyl glycopyranoside) were prepared by acetalization or transacetalization of sugars following the procedure previously described in patent Ser. No. 13/01,375 "Method for preparing long-chain alkyl cyclic acetals made from sugars." The alkyl sugar acetals are then reduced using reduction conditions without an acid catalyst previously described in patent Ser. No. 14/01,346. The method used is the same for the case of alkyl acetals sorbitan and alkyl acetals of methyl glycopyranosides. For indication, the synthesis of acetals and ethers is described below.

Example 1: General Procedure for the Preparation of Methyl Glycopyranoside Alkyl Acetals (A)

In a 100-mL round-bottomed flask, under an argon atmosphere, methyl glycopyranoside (2 equivalents) is dissolved in dry THF (10 mL) in the presence of sodium sulfate (1.5 equivalents). The aldehyde (1 equivalent) is added dropwise over one minute, followed by Amberlyst 15 (20% by mass relative to the aldehyde). The reaction mixture is stirred magnetically at reflux (65° C.) for 3 hours. After returning to ambient temperature, the reaction mixture is filtered, washed with ethyl acetate (2×25 mL) and the filtrate is concentrated under low pressure. The residue is purified by chromatography on a silica gel column (AcOEt/cyclohexane) to give the methyl glycopyranoside alkyl acetals.

Example 1a

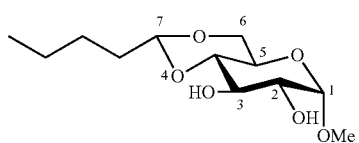

Methyl 4,6-O-pentylidene α-D-glucopyranoside (1a): Compound 1a was prepared from methyl α-D-glucopyranoside (7.49 g, 38.5 mmol) and pentanal (1.64 g, 19 mmol) according to procedure (A). After reaction, the residue was purified by chromatography on silica gel column (EtOAc/cyclohexane, 80:20) to give 1a (2.14 g, 43%) in the form of a white solid. Melting point=78° C.; NMR $^1$H (300 MHz, CDCl$_3$) $\delta_H$: 0.88 (3H, t, J=7, CH$_3$ alkyl), 1.21-1.44 (4H, m, 2(CH$_2$) alkyl), 1.52-1.72 (2H, m, CH$_2$ alkyl), 2.80 (1H, d, J=9, OH$^3$), 3.23 (1H, t, J=9, H$^3$), 3.31 (1H, d, J=2, OH$^2$), 3.40 (3H, s, OCH$_3$), 3.48 (1H, t, J=10, H$^2$), 3.52-3.67 (2H, m, H$^5$+H$^6$), 3.83 (1H, td, J=9 and 2, H$^4$), 4.09 (1H, dd, J=10 and 4, H$^6$), 4.52 (1H, t, J=5, H$^7$), 4.73 (1H, d, J=4, H$^1$); NMR $^{13}$C (75 MHz, CDCl$_3$) $\delta_C$: 14.05 (CH$_3$), 22.62 (CH$_2$), 26.30 (CH$_2$), 34.03 (CH$_2$), 55.54 (OCH$_3$), 62.62 (CH$^5$), 68.57 (CH$_2^6$), 71.70 (CH$^4$), 72.98 (CH$^2$), 80.47 (CH$^3$), 99.87 (CH$^1$), 102.81 (CH$^7$). IR $\nu_{max}$: 3399 (OH), 2956, 2862, 1428, 1390, 1062, 1041, 989; HRMS (ESI$^+$) calculated for C$_{12}$H$_{22}$NaO$_6$: 285.1309 [M+Na]$^+$, measured: 285.1315 (−2.2 ppm); Rf=0.27 (EtOAc/cyclohexane 80:20).

Example 1b

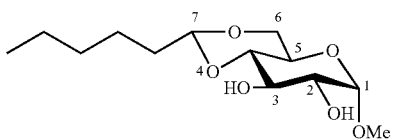

Methyl 4,6-O-Hexylidene α-D-glucopyranoside (1b): Compound 1b was prepared from methyl α-D-glucopyranoside (3.22 g, 16.6 mmol) and hexanal (0.83 g, 8.3 mmol) according to procedure (A). After reaction, the residue was purified by chromatography on silica gel column (EtOAc/cyclohexane, 80:20) to give 1b (0.98 g, 43%) in the form of a white solid. Melting point=84° C.; NMR $^1$H (300 MHz, CDCl$_3$) $\delta_H$: 0.86 (3H, t, J=7, CH$_3$ alkyl), 1.05-1.30 (4H, m, 2(CH$_2$) alkyl), 1.31-1.46 (2H, m, CH$_2$ alkyl), 1.52-1.74 (2H, m, CH$_2$ alkyl), 3.02 (1H, br s, OH$^3$), 3.23 (1H, t, J=9, H$^3$), 3.40 (3H, s, OCH$_3$), 3.47 (1H, t, J=10, H$^2$), 3.52-3.66 (2H, m, H$^5$+H$^6$), 3.83 (1H, t, J=9, H$^4$), 4.09 (1H, dd, J=10 and 5, H$^6$), 4.52 (1H, t, J=5, H$^7$), 4.72 (1H, d, J=4, H$^1$); NMR $^{13}$C (75 MHz, CDCl$_3$) $\delta_C$: 14.10 (CH$_3$), 22.62 (CH$_2$), 23.86 (CH$_2$), 31.74 (CH$_2$), 34.28 (CH$_2$), 55.51 (OCH$_3$), 62.62 (CH$^5$), 68.56 (CH$_2^6$), 71.61 (CH$^4$), 72.95 (CH$^2$), 80.49 (CH$^3$), 99.90 (CH$^1$), 102.81 (CH$^7$); IR $\nu_{max}$: 3433 (OH), 2925 (—CH$_3$), 2860 (—CH$_2$—), 1465, 1379, 1061, 983; HRMS (ESI$^+$) calculated for C$_{13}$H$_{24}$NaO$_6$: 299.1465 [M+Na]$^+$; measured: 299.1464 (+0.4 ppm); Rf=0.27 (80:20 EtOAc/cyclohexane).

Example 1c

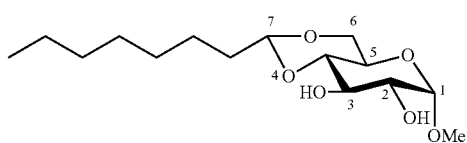

Methyl 4,6-O-Octylidene α-D-glucopyranoside (1c): Compound 1c was prepared from methyl α-D-glucopyranoside (3.22 g, 16.6 mmol) and octanal (1.06 g, 8.3 mmol) according to procedure (A). After reaction, the residue was purified by chromatography on silica gel column (EtOAc/cyclohexane, 50:50) to give 1c (0.94 g, 37%) in the form of a white solid. Melting point=80° C.; NMR $^1$H (300 MHz, CDCl$_3$) $\delta_H$: 0.85 (3H, t, J=7, CH$_3$ alkyl), 1.07-1.31 (8H, m, 4(CH$_2$) alkyl), 1.32-1.47 (2H, m, CH$_2$ alkyl), 1.50-1.73 (2H, m, CH$_2$ alkyl), 3.02 (2H, br s, OH$^2$+OH$^3$), 3.23 (1H, t, J=9, H$^3$), 3.40 (3H, s, OCH$_3$), 3.48 (1H, t, J=10, H$^2$), 3.52-3.67 (2H, m, H$^5$), 3.83 (1H, t, J=9, H$^4$), 4.09 (1H, dd, J=10 and 5, H$^6$), 4.52 (1H, t, J=5, H$^7$), 4.72 (1H, d, J=4, H$^1$); NMR $^{13}$C (75 MHz, CDCl$_3$) $\delta_C$: 14.18 (CH$_3$), 22.73 (CH$_2$), 24.18 (CH$_2$), 29.26 (CH$_2$), 29.51 (CH$_2$), 31.85 (CH$_2$), 34.33 (CH$_2$), 55.53 (OCH$_3$), 62.62 (CH$^5$), 68.56 (CH$_2^6$), 71.68 (CH$^4$), 72.97 (CH$^2$), 80.48 (CH$^3$), 99.88 (CH), 102.82 (CH$^7$); IR $\nu_{max}$: 3368 (OH), 2924, 2857, 1465, 1378, 1128, 1090, 1064, 1037, 993; HRMS (ESI$^+$) calculated for C$_{15}$H$_{28}$NaO$_6$: 327.1778 [M+Na]$^+$; measured: 327.1780 (−0.6 ppm); Rf=0.21 (50:50 EtOAc/cyclohexane).

Example 1d

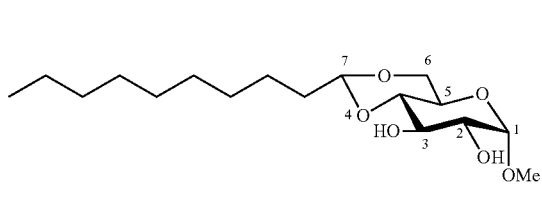

Methyl 4,6-O-Decylidene α-D-glucopyranoside (1d): Compound 1d was prepared from methyl α-D-glucopyranoside (20 g, 102 mmol) and decanal (7.97 g, 51 mmol) according to procedure (A). After reaction, the residue was purified by chromatography on silica gel column (EtOAc/cyclohexane, 80:20) to give 1d (7.48 g, 44%) in the form of a white solid. Melting point=72° C.; NMR $^1$H (300 MHz, CDCl$_3$) δ$_H$: 0.87 (3H, t, J=7, CH$_3$ alkyl), 1.16-1.32 (12H, m, 6(CH$_2$) alkyl), 1.33-1.45 (2H, m, CH$_2$ alkyl), 1.55-1.72 (2H, m, CH$_2$ alkyl), 2.61 (2H, br s, OH$^3$+OH$^2$), 3.24 (1H, t, J=9, H$^3$), 3.42 (3H, s, OCH$_3$), 3.49 (1H, t, J=10, H$^2$), 3.53-3.68 (2H, m, H$^5$), 3.84 (1H, t, J=9, H$^4$), 4.11 (1H, dd, J=10 and 5, H$^6$), 4.53 (1H, t, J=5, H$^7$), 4.74 (1H, d, J=4, H$^1$); NMR $^{13}$C (75 MHz, CDCl$_3$) δ$_C$: 14.03 (CH$_3$), 22.59 (CH$_2$), 24.08 (CH$_2$), 29.25 (CH$_2$), 29.46 (CH$_2$), 29.49 (2CH$_2$), 31.82 (CH$_2$), 34.19 (CH$_2$), 55.20 (OCH$_3$), 62.54 (CH$^5$), 68.43 (CH$_2^6$), 70.90 (CH$^4$), 72.65 (CH$^2$), 80.53 (CH$^3$), 100.02 (CH$^1$), 102.64 (CH$^7$); IR v$_{max}$: 3393 (OH), 2922, 2853, 1466, 1378, 1112, 1088, 1063, 1037, 990; HRMS (ESI$^+$) calculated for C$_{17}$H$_{32}$NaO$_6$: 355.2091 [M+Na]$^+$; measured: 355.2102 (−3.2 ppm); Rf=0.32 (80:20 EtOAc/cyclohexane).

Example 1e

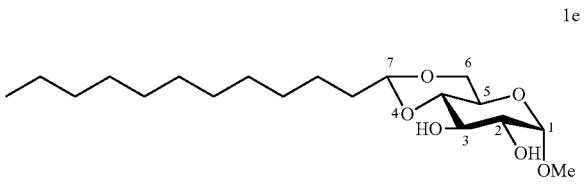

Methyl 4,6-O-Dodecylidene α-D-glucopyranoside (1e): Compound 1e was prepared from methyl α-D-glucopyranoside (3.22 g, 16.6 mmol) and dodecanal (1.52 g, 8.3 mmol) according to procedure (A). After reaction, the residue was purified by chromatography on silica gel column (EtOAc/cyclohexane 60:40) to give 1d (0.77 g, 26%) in the form of a white solid. Melting point=69° C.; NMR $^1$H (300 MHz, CDCl$_3$) δ$_H$: 0.86 (3H, t, J=7, CH$_3$), 1.17-1.32 (16H, m, 8CH$_2$), 1.33-1.47 (2H, m, CH$_2$), 1.53-1.74 (2H, m, CH$_2$), 2.64 (2H, br s, OH$^3$+OH$^2$), 3.24 (1H, t, J=9.0, CH$^3$), 3.41 (3H, s, OCH$_3$), 3.49-3.68 (3H, m, CH$^5$+CH$^6$+CH$^2$), 3.84 (1H, t, J=9.0, CH$^4$), 4.10 (1H, dd, J=10.0 and 5.0, CH$^6$), 4.52 (1H, t, J=5.0, CH$^7$), 4.74 (1H, d, J=4.0, CH); NMR $^{13}$C (75 MHz, CDCl$_3$) δ$_C$: 14.24 (CH$_3$), 22.80 (CH$_2$), 24.20 (CH$_2$), 29.46 (CH$_2$), 29.58 (CH$_2$), 29.62 (CH$_2$), 29.67 (CH$_2$), 29.74 (CH$_2$), 29.76 (CH$_2$), 32.03 (CH$_2$), 34.36 (CH$_2$), 55.57 (OCH$_3$), 62.63 (CH$^5$), 68.57 (CH$_2^6$), 71.81 (CH$^4$), 73.02 (CH$^2$), 80.46 (CH$^3$), 99.85 (CH), 102.84 (CH$^7$); IR v$_{max}$: 3388 (OH), 2921, 2852, 1466, 1378, 1089, 1063, 1037, 991; HRMS (ESI$^+$) calculated for C$_{19}$H$_{36}$NaO$_6$: 383.2404 [M+Na]$^+$; measured: 383.2398 (+1.6 ppm); Rf=0.30 (EtOAc/cyclohexane 60:40).

Example 1f

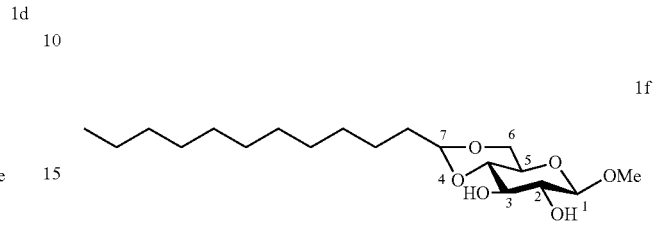

Methyl 4,6-O-Dodecylidene β-D-glucopyranoside (1f): Compound 1f was prepared from methyl β-D-glucopyranoside (5.00 g, 25.7 mmol) and dodecanal (2.37 g, 12.8 mmol) according to procedure (A). After reaction, the residua was purified by silica gel column chromatography (EtOAc/cyclohexane, from 30:70 to 50:50) to give 1f (1.30 g, 28%) in the form of a white solid. Melting point=84° C.; NMR $^1$H (300 MHz, CDCl$_3$) δ$_H$: 0.87 (3H, t, J=6.7, CH$_3$), 1.25 (16H, app br s, 8CH$_2$), 1.34-1.45 (2H, m, CH$_2$), 1.53-1.73 (2H, m, CH$_2$), 3.25-3.34 (2H, m, CH$^2$+CH$^5$), 3.44 (1H, dd, J=9.0, 7.0, CH$^3$), 3.56 (4H, s, CH$_2^6$+OCH$_3$), 3.73 (1H, m, CH$^4$), 4.18 (1H, dd, J=10.4, 4.4, CH$_2^6$), 4.28 (1H, d, J=7.7, CH$^1$), 4.54 (1H, t, J=5.1, CH$^7$); NMR $^{13}$C (75 MHz, CDCl$_3$) δ$_C$: 14.13 (CH$_3$), 22.70 (CH$_2$), 24.14 (CH$_2$), 29.35 (CH$_2$), 29.45 (CH$_2$), 29.50 (CH$_2$), 29.56 (CH$_2$), 29.63 (CH$_2$), 29.65 (CH$_2$), 31.92 (CH$_2$), 34.23 (CH$_2$), 55.51 (OCH$_3$), 66.21 (CH$^5$), 68.21 (CH$_2^6$), 73.19 (CH$^4$), 74.61 (CH$^2$), 80.00 (CH$^3$), 102.83 (CH$^7$), 104.07 (CH); IR v$_{max}$: 3650 (OH), 2950, 2824, 2867, 2159, 2028, 1112; HRMS (ESI$^+$) calculated for C$_{19}$H$_{36}$NaO$_6$: 383.2404 [M+Na]$^+$; measured: 383.2395 (+2.3 ppm). Rf=0.30 (EtOAc/cyclohexane 40:60)

Example 1g

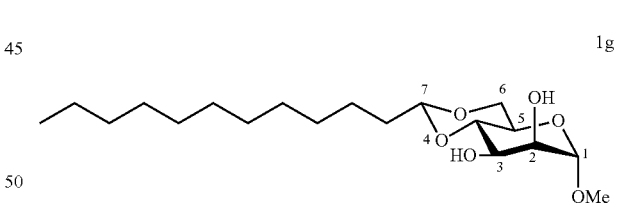

Methyl 4,6-O-Dodecylidene α-D-mannopyranoside (1g): Compound 1g was prepared from methyl α-D-mannopyranoside (4.00 g, 20.5 mmol) and dodecanal (3.45 g, 18.7 mmol) according to procedure (A). After reaction, the reaction medium is concentrated under low pressure and dissolved in the CH$_2$Cl$_2$. The organic phase is washed with water (3×100 mL), with a saturated NaCl solution (2×100 mL), dried (Na$_2$SO$_4$) and concentrated under low pressure. The residua was purified by silica gel column chromatography (EtOAc/cyclohexane, from 20:80 to 50:50) to give 1g (0.73 g, 11%) in the form of a white solid. Melting point=104° C.; NMR $^1$H (300 MHz, CDCl$_3$) δ$_H$: 0.88 (3H, t, J=6.9, CH$_3$), 1.17-1.32 (16H, m, 8CH$_2$), 1.37-1.42 (2H, m, CH$_2$), 1.58-1.68 (2H, m, CH$_2$), 3.37 (3H, s, OCH$_3$), 3.53-3.72 (3H, m, CH$^3$+CH$^5$+CH$^6$), 3.98 (1H, dd, J=9.0, 3.7, CH²), 4.13 (1H, dd, J=3.6, 1.4, CH⁴), 4.58 (1H, dd, J=8.8, 2.9, CH⁶), 4.10 (1H, t, J=5.1, CH⁷), 4.73 (1H, d, J=1.3, CH¹); NMR $^{13}$C (75 MHz, CDCl$_3$) $\delta_C$: 14.13 (CH$_3$), 22.69 (CH$_2$), 24.10 (CH$_2$), 29.35 (CH$_2$), 29.46 (CH$_2$), 29.51 (CH$_2$), 29.56 (CH$_2$), 29.63 (CH$_2$), 29.65 (CH$_2$), 31.92 (CH$_2$), 34.40 (CH$_2$), 55.05 (OCH$_3$), 63.00 (CH⁵), 68.38 (CH$_2$⁶), 68.81 (CH²), 70.82 (CH⁴), 78.23 (CH³), 101.15 (CH), 103.06 (CH⁷); IR $\nu_{max}$: 3380 (OH), 2924, 2852, 1466, 1156, 1029, 682; HRMS (ESI⁺) calculated for C$_{19}$H$_{36}$NaO$_6$: 383.2404 [M+Na]⁺; measured: 383.2396 (+2.2 ppm). Rf=0.2 (cyclohexane/EtOAc, 70:30).

Example 1h

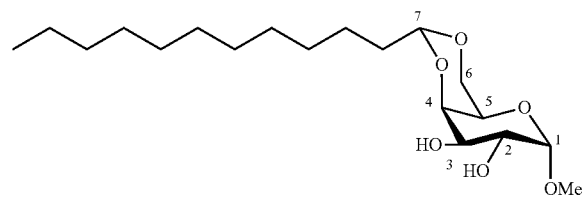

1h

Methyl 4,6-O-Dodecylidene α-D-galactopyranoside (1h): Compound 1h was prepared from methyl α-D-galactopyranoside (5.00 g, 25.7 mmol) and dodecanal (2.37 g, 12.9 mmol) according to procedure (A). After reaction, the reaction medium is concentrated under low pressure to give 1h (2.30 g, 45%) in the form of a white solid without purification by chromatography. Melting point=115° C.; NMR $^1$H (300 MHz, CDCl$_3$) $\delta_H$: 0.89 (3H, t, J=6.7, CH$_3$), 1.15-1.50 (18H, m, 9CH$_2$), 1.61-1.71 (2H, m, CH$_2$), 3.45 (3H, s, OCH$_3$), 3.61 (1H, app. s, CH⁵), 3.77-3.94 (3H, m, CH⁴+CH²CH⁶), 4.04 (1H, d, J=2.5, H³), 4.14 (1H, dd, J=12.5, 1.4, CH⁶), 4.59 (1H, t, J=5.2, CH⁷), 4.91 (1H, d, J=3.2, CH¹); NMR $^{13}$C (75 MHz, CDCl$_3$) $\delta_C$: 14.06 (CH$_3$), 22.50 (CH$_2$), 23.49 (CH$_2$), 29.27 (CH$_2$), 29.34 (CH$_2$), 29.41 (CH$_2$), 29.48 (CH$_2$), 29.55 (CH$_2$), 29.61 (CH$_2$), 31.97 (CH$_2$), 34.47 (CH$_2$), 55.66 (OCH$_3$), 62.45 (CH⁵), 68.92 (CH$_2$⁶), 69.82 (CH²), 69.92 (CH⁴), 75.42 (CH³), 100.1 (CH⁷), 102.1 (CH); IR $\nu_{max}$: 3414, 3328 (OH), 2916, 2850, 2160, 1121, 1032; HRMS (ESI⁺) calculated for C$_{19}$H$_{36}$NaO$_6$ 383.2404 [M+Na]⁺; measured: 383.2389 (+4.0 ppm). Rf=0.6 (EtOAc/cyclohexane, 60:40).

Example 2: General Procedure for the Preparation of Mixtures of Regioisomers of Methyl Glycopyranoside Alkyl Ethers (B)

In a 100-mL stainless-steel autoclave, the methyl glycopyranoside alkyl acetal (3 mmol) is dissolved in cyclopentylmethylether (CPME, 30 mL) and 5%-Pd/C (0.45 g, 5% molar in palladium) is then added. The reactor is hermetically sealed, purged three times with hydrogen then hydrogen is introduced to a pressure of 30 bars. The reaction mixture is stirred mechanically and heated to 120° C. for 15 hours. After cooling to ambient temperature, the hydrogen pressure is released and the reaction mixture is diluted in absolute ethanol (100 mL) and filtered (Millipore Durapore 0.01 μm filter). The filtrate is concentrated under low pressure to give the mixture of regioisomers of methyl glycopyranoside alkyl ethers.

Example 2a

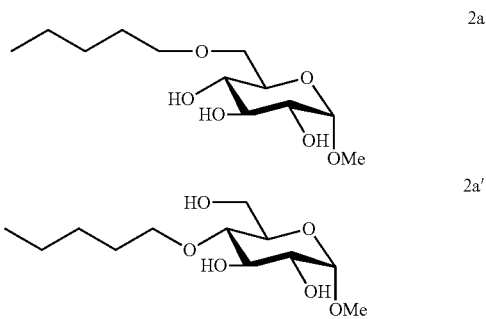

Methyl 6-O-Pentyl α-D-glucopyranoside (2a) and methyl 4-O-pentyl α-D-glucopyranoside (2a'): Compounds 2a and 2a' were prepared from methyl 4,6-O-pentylidene α-D-glucopyranoside 1a (4.00 g, 15 mmol) according to the general procedure (B). A 70:30 mixture of 2a and 2a' (1.51 g, 38%) is obtained in the form of a white paste. To facilitate compound characterization, the regioisomers in the mixture may be separated by silica gel column chromatography (EtOAc/cyclohexane, from 50:50 to 100:0 then EtOH/EtOAc 10:90). 2a: Colorless oil. NMR $^1$H (300 MHz, CDCl$_3$) $\delta_H$: 0.84 (3H, t, J=7, CH$_3$ alkyl), 1.14-1.36 (4H, m, 2(CH$_2$) alkyl), 1.41-1.68 (2H, m, CH$_2$ alkyl), 3.34 (3H, s, OCH$_3$), 3.40-3.82 (7H, m), 4.53-4.81 (4H, m, CH-anomeric+3OH); NMR $^{13}$C (75 MHz, CDCl$_3$) $\delta_C$: 14.06 (CH$_3$), 22.53 (CH$_2$), 28.20 (CH$_2$), 29.29 (CH$_2$), 55.12 (OCH$_3$), 70.20 (CH$_2$), 70.57 (CH), 70.74 (CH), 71.91 (CH), 72.05 (CH$_2$), 74.26 (CH), 99.56 (CH); IR $\nu_{max}$: 3382 (OH), 2929, 2861, 1455, 1363, 1192, 1144, 1108, 1040, 900; HRMS (ESI⁺) calculated for C$_{12}$H$_{24}$NaO$_6$: 287.1465 [M+Na]⁺; measured: 287.1467 (−0.8 ppm); Rf=0.35 (EtOAc/EtOH 10:1). 2a': Colorless oil. NMR $^1$H (300 MHz, CDCl$_3$) $\delta_H$: 0.86 (3H, t, J=7, CH$_3$ alkyl), 1.16-1.38 (4H, m, 2(CH$_2$) alkyl), 1.42-1.66 (2H, m, CH$_2$ alkyl), 3.16 (3H, br s, OH), 3.21 (1H, t, J=10), 3.37 (3H, s, OCH$_3$), 3.42-3.87 (7H, m), 4.71 (1H, d, J=3, CH anomeric); NMR $^{13}$C (75 MHz, CDCl$_3$) $\delta_C$: 14.11 (CH$_3$), 22.61 (CH$_2$), 28.26 (CH$_2$), 30.05 (CH$_2$), 55.32 (OCH$_3$), 61.92 (CH$_2$), 71.00 (CH), 72.61 (CH), 73.14 (CH$_2$), 74.52 (CH), 77.86 (CH), 99.35 (CH); IR $\nu_{max}$: 3388 (OH), 2928, 2852, 1452, 1371, 1092, 1083, 1037, 931; HRMS (ESI⁺) calculated for C$_{12}$H$_{24}$NaO$_6$: 287.1465 [M+Na]⁺; measured: 287.1465 (+0.2 ppm); Rf=0.40 (EtOAc/EtOH 10:1).

Example 2b

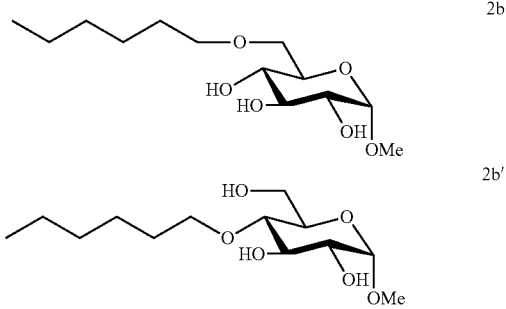

Methyl 6-O-Hexyl α-D-glucopyranoside (2b) and methyl 4-O-hexyl α-D-glucopyranoside (2b'): Compounds 2b and 2b' were prepared from methyl 4,6-O-hexylidene α-D-glucopyranoside 1b (5.50 g, 20 mmol) according to the general procedure (B). A 72:28 mixture of 2b and 2b' (2.18 g, 37%) was obtained in the form of a colorless oil. To facilitate compound characterization, the regioisomers in the mixture may be separated by silica gel column chromatography (EtOAc/cyclohexane, from 50:50 to 100:0 then EtOH/EtOAc 10:90). 2b: Colorless oil. NMR $^1$H (300 MHz, CDCl$_3$) $\delta_H$: 0.84 (3H, t, J=7, CH$_3$ alkyl), 1.13-1.38 (6H, m, 3(CH$_2$) alkyl), 1.44-1.64 (2H, m, CH$_2$ alkyl), 3.38 (3H, s, OCH$_3$), 3.39-3.78 (8H, m), 4.53 (3H, br s, OH), 4.71 (1H, d, J=4, CH-anomeric); NMR $^{13}$C (75 MHz, CDCl$_3$) $\delta_C$: 14.10 (CH$_3$), 22.66 (CH$_2$), 25.75 (CH$_2$), 29.60 (CH$_2$), 31.75 (CH$_2$), 55.18 (OCH$_3$), 70.24 (CH$_2$), 70.55 (CH), 70.79 (CH), 71.94 (CH), 72.13 (CH$_2$), 74.28 (CH), 99.56 (CH); IR $\nu_{max}$: 3376 (OH), 2928, 2859, 1455, 1364, 1192, 1144, 1006, 1043, 900; HRMS (ESI$^+$) calculated for C$_{13}$H$_{26}$NaO$_6$: 301.1622 [M+Na]$^+$; measured: 301.1612 (+3.3 ppm); Rf=0.32 (EtOAc/EtOH 10:1). 2b': Colorless oil. NMR $^1$H (300 MHz, CDCl$_3$) $\delta_H$: 0.87 (3H, t, J=7, CH$_3$ alkyl), 1.17-1.40 (6H, m, 3(CH$_2$) alkyl), 1.46-1.66 (2H, m, CH$_2$ alkyl), 2.43-2.78 (3H, br s, OH), 3.23 (1H, t, J=10), 3.39 (3H, s, OCH$_3$), 3.48 (1H, dd, J=10 and 4), 3.53-3.64 (2H, m), 3.64-3.91 (4H, m), 4.73 (1H, d, J=4, CH-anomeric); NMR $^{13}$C (75 MHz, CDCl$_3$) $\delta_c$: 14.16 (CH$_3$), 22.72 (CH$_2$), 25.83 (CH$_2$), 30.38 (CH$_2$), 31.80 (CH$_2$), 55.41 (OCH$_3$), 62.05 (CH$_2$), 71.00 (CH), 72.72 (CH), 73.24 (CH$_2$), 74.80 (CH), 77.91 (CH), 99.27 (CH); IR $\nu_{max}$: 3395 (OH), 2927, 2852, 1456, 1365, 1192, 1114, 1027, 896; HRMS (ESI$^+$) calculated for C$_{13}$H$_{26}$NaO$_6$: 301.1622 [M+Na]$^+$; measured: 301.1610 (+4.0 ppm); Rf=0.38 (EtOAc/EtOH 10:1).

Example 2c

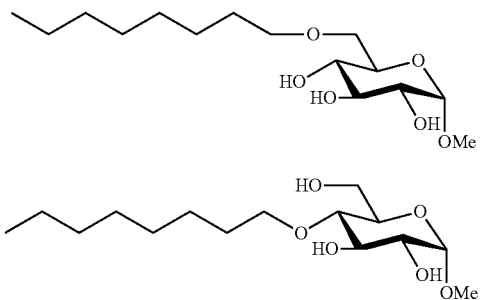

Methyl 6-O-Octyl α-D-glucopyranoside (2c) and methyl 4-O-octyl α-D-glucopyranoside (2c'): Compounds 2c and 2c' have been prepared from methyl 4,6-O-octylidene α-D-glucopyranoside 1c (5.00 g, 16.4 mmol) according to the general procedure (B). A 75:25 mixture of 2c and 2c' (2.30 g, 40%) was obtained in the form of a colorless oil. To facilitate compound characterization, the regioisomers in the mixture may be separated by silica gel column chromatography (EtOAc/cyclohexane, from 50:50 to 100:0 then EtOH/EtOAc 10:90). 2c: Colorless oil. NMR $^1$H (300 MHz, CDCl$_3$) $\delta_H$: 0.86 (3H, t, J=7, CH$_3$ alkyl), 1.15-1.38 (10H, m, 5(CH$_2$) alkyl), 1.48-1.68 (2H, m, CH$_2$ alkyl), 3.40 (3H, s, OCH$_3$), 3.42-3.92 (8H, m), 4.22 (3H, br s, OH), 4.73 (1H, d, J=4, CH-anomeric); NMR $^{13}$C (75 MHz, CDCl$_3$) $\delta_C$: 14.22 (CH$_3$), 22.78 (CH$_2$), 26.15 (CH$_2$), 29.39 (CH$_2$), 29.59 (CH$_2$), 29.72 (CH$_2$), 31.96 (CH$_2$), 55.30 (OCH$_3$), 70.44 (CH$_2$), 71.12 (CH), 72.08 (CH), 72.24 (CH), 74.44 (CH$_2$), 77.36 (CH), 99.60 (CH); IR $\nu_{max}$: 3371 (OH), 2923, 2854, 1456, 1365, 1192, 1144, 1108, 1044, 900; HRMS (ESI$^+$) calculated for C$_{15}$H$_{30}$NaO$_6$: 329.1935 [M+Na]$^+$; measured: 329.1943 (−2.5 ppm); Rf=0.26 (EtOAc/EtOH 10:1). 2c': White solid. NMR $^1$H (300 MHz, CDCl$_3$) $\delta_H$: 0.86 (3H, t, J=7, CH$_3$ alkyl), 1.09-1.39 (10H, m, 5(CH$_2$) alkyl), 1.43-1.66 (2H, m, CH$_2$ alkyl), 2.58 (3H, br s, OH), 3.23 (1H, t, J=10); 3.39 (3H, s, OCH$_3$), 3.48 (1H, dd, J=10 and 4), 3.53-3.64 (2H, m), 3.66-3.89 (4H, m), 4.73 (1H, d, J=4, CH-anomeric); NMR $^{13}$C (75 MHz, CDCl$_3$) $\delta_C$: 14.20 (CH$_3$), 22.76 (CH$_2$), 26.18 (CH$_2$), 29.37 (CH$_2$), 29.58 (CH$_2$), 30.44 (CH$_2$), 31.93 (CH$_2$), 55.41 (OCH$_3$), 62.08 (CH$_2$), 71.01 (CH), 72.75 (CH), 73.25 (CH$_2$), 74.84 (CH), 77.94 (CH), 99.28 (CH); IR $\nu_{max}$: 3388 (OH), 2922, 2853, 1456, 1365, 1192, 1144, 1110, 1045, 899; HRMS (ESI$^+$) calculated for C$_{15}$H$_{30}$NaO$_6$: 329.1935 [M+Na]$^+$; measured: 329.1935 (−0.2 ppm); Rf=0.38 (EtOAc/EtOH 10:1).

Example 2d

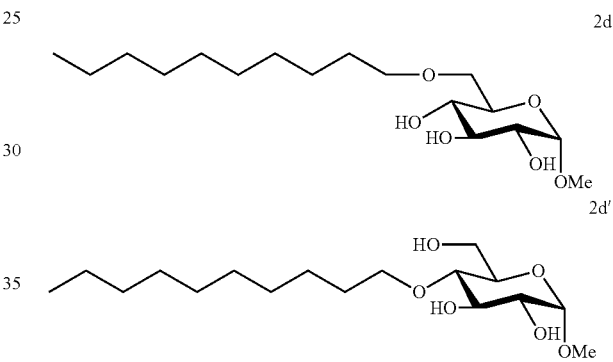

Methyl 6-O-Decyl α-D-glucopyranoside (2d) and methyl 4-O-decyl α-D-glucopyranoside (2d'): Compounds 2d and 2d' were prepared from methyl 4,6-O-decylidene α-D-glucopyranoside 1d (6.00 g, 18 mmol) according to the general procedure (B). A 77:23 mixture of 2d and 2d' (1.52 g, 25%) was obtained in the form of a white paste. To facilitate compound characterization, the regioisomers in the mixture may be separated by silica gel column chromatography (EtOAc/cyclohexane, from 50:50 to 100:0 then EtOH/EtOAc 10:90). 2d: Colorless oil. NMR $^1$H (300 MHz, CDCl$_3$) $\delta_H$: 0.86 (3H, t, J=7, CH$_3$ alkyl), 1.11-1.38 (14H, m, 7(CH$_2$) alkyl), 1.47-1.66 (2H, m, CH$_2$ alkyl), 3.40 (3H, s, OCH$_3$), 3.42-3.89 (8H, m), 4.32 (3H, br s, OH), 4.73 (1H, d, J=4, CH-anomeric); NMR $^{13}$C (75 MHz, CDCl$_3$) $\delta_C$: 14.22 (CH$_3$), 22.79 (CH$_2$), 26.15 (CH$_2$), 29.45 (CH$_2$), 29.65 (CH$_2$), 29.72 (2CH$_2$), 29.74 (CH$_2$), 32.02 (CH$_2$), 55.27 (OCH$_3$), 70.41 (CH$_2$), 70.48 (CH), 71.02 (CH), 72.04 (CH), 72.23 (CH$_2$), 74.40 (CH), 99.60 (CH); IR $\nu_{max}$: 3400 (OH), 2919, 2852, 1467, 1369, 1123, 1043, 1014, 901; HRMS (ESI$^+$) calculated for C$_{17}$H$_{34}$NaO$_6$: 357.2248 [M+Na]$^+$; measured: 357.2247 (+0.1 ppm); Rf=0.30 (EtOAc/EtOH 10:1). 4d: White solid. NMR $^1$H (300 MHz, CDCl$_3$) $\delta_H$: 0.88 (3H, t, J=7, CH$_3$alkyl), 1.10-1.39 (14H, m, 7(CH$_2$) alkyl), 1.47-1.68 (2H, m, CH$_2$ alkyl), 2.13 (4H, br s, OH+H), 3.25 (1H, t, J=10); 3.41 (3H, s, OCH$_3$), 3.48 (1H, dd, J=10 and 4), 3.54-3.68 (2H, m), 3.69-3.94 (3H, m), 4.75 (1H, d, J=4, CH-anomeric); NMR $^{13}$C (75 MHz, CDCl$_3$) $\delta_C$: 14.25 (CH$_3$), 22.82 (CH$_2$), 26.21 (CH$_2$), 29.45 (CH$_2$), 29.63

(CH$_2$), 29.70 (CH$_2$), 29.73 (CH$_2$), 30.47 (CH$_2$), 32.02 (CH$_2$), 55.47 (OCH$_3$), 62.18 (CH$_2$), 70.99 (CH), 72.82 (CH), 73.28 (CH$_2$), 75.08 (CH), 77.95 (CH), 99.19 (CH); IR $v_{max}$: 3370 (OH), 2923, 2853, 1466, 1370, 1317, 1192, 1112, 1070, 1050, 899; HRMS (ESI$^+$) calculated for C$_{17}$H$_{34}$NaO$_6$: 357.2248 [M+Na]$^+$; measured: 357.2252 (−1.2 ppm); Rf=0.38 (EtOAc/EtOH 10:1).

Example 2e

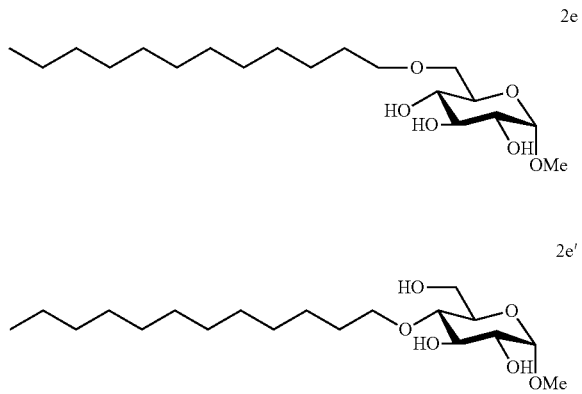

Methyl 6-O-Dodecyl α-D-glucopyranoside (2e) and methyl 4-O-dodecyl α-D-glucopyranoside (2e'): Compounds 2e and 2e' were prepared from methyl 4,6-O-dodecylidene α-D-glucopyranoside 1e (5.00 g, 14 mmol) according to the general procedure (B). A 73:27 mixture of 2e and 2e' (2.52 g, 51%) was obtained in the form of a white solid. To facilitate compound characterization, the regioisomers in the mixture may be separated by silica gel column chromatography (EtOAc/cyclohexane, from 50:50 to 100:0 then EtOH/EtOAc 10:90). 2e: White solid. NMR $^1$H (300 MHz, CDCl$_3$) $\delta_H$: 0.87 (3H, t, J=7, CH$_3$ alkyl), 1.09-1.44 (18H, m, 9(CH$_2$) alkyl), 1.47-1.70 (2H, m, CH$_2$ alkyl), 3.41 (3H, s, OCH$_3$), 3.43-3.84 (7H, m), 4.21 (3H, br s, OH), 4.74 (1H, d, J=4, CH-anomeric); NMR $^{13}$C (75 MHz, CDCl$_3$) $\delta_C$: 14.25 (CH$_3$), 22.82 (CH$_2$), 26.17 (CH$_2$), 29.50 (CH$_2$), 29.67 (CH$_2$), 29.73 (CH$_2$), 29.77 (CH$_2$), 29.80 (2CH$_2$), 29.83 (CH$_2$), 32.06 (CH$_2$), 55.35 (OCH$_3$), 70.33 (CH), 70.51 (CH$_2$), 71.23 (CH), 72.10 (CH), 72.30 (CH$_2$), 74.49 (CH), 99.57 (CH); IR $v_{max}$: 3402 (OH), 2918, 2851, 1467, 1370, 1057, 1015, 902; HRMS (ESI$^+$) calculated for C$_{19}$H$_{38}$NaO$_6$: 385.2561 [M+Na]$^+$; measured: 385.2558 (+0.6 ppm); Rf=0.16 (EtOAc/EtOH 10:1). 2e': white solid. NMR $^1$H (300 MHz, CDCl$_3$) $\delta_H$: 0.87 (3H, t, J=7, CH$_3$ alkyl), 1.14-1.42 (18H, m, 9(CH$_2$) alkyl), 1.47-1.71 (2H, m, CH$_2$ alkyl), 2.16 (3H, br s, OH), 3.24 (1H, t, J=10); 3.41 (3H, s, OCH$_3$), 3.49 (1H, dd, J=10 and 4), 3.54-3.66 (2H, m), 3.69-3.91 (4H, m), 4.74 (1H, d, J=4, CH-anomeric); NMR $^{13}$C (75 MHz, CDCl$_3$) $\delta_C$: 14.26 (CH$_3$), 22.83 (CH$_2$), 26.20 (CH$_2$), 29.49 (CH$_2$), 29.64 (CH$_2$), 29.74 (2CH$_2$), 29.77 (CH$_2$), 29.80 (CH$_2$), 30.47 (CH$_2$), 32.06 (CH$_2$), 55.46 (OCH$_3$), 62.15 (CH$_2$), 70.99 (CH), 72.81 (CH), 73.28 (CH$_2$), 75.05 (CH), 77.94 (CH), 99.20 (CH); IR $v_{max}$: 3295 (OH), 2913, 2848, 1739, 1469, 1370, 1114, 1067, 1042, 993; HRMS (ESI$^+$) calculated for C$_{19}$H$_{38}$NaO$_6$: 385.2561 [M+Na]$^+$; measured: 385.2574 (−3.5 ppm); Rf=0.24 (EtOAc/EtOH 10:1).

Example 2f

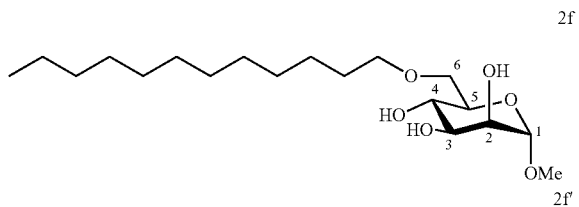

Methyl 6-O-Dodecyl α-D-mannopyranoside (2f) and methyl 4-O-dodecyl α-D-mannopyranoside (2f'): Compounds 2f and 2f' were prepared from methyl 4,6-O-dodecylidene α-D-mannopyranoside 1g (0.70 g, 1.94 mmol) according to the general procedure (B). After reaction, the residue was purified by chromatography on silica gel column (EtOAc/cyclohexane, 40:60). An inseparable 75:25 mixture of 2f and 2f' (0.24 g, 34%) was obtained in the form of a colorless oil. NMR $^1$H (300 MHz, CDCl$_3$) $\delta_H$ for the main regioisomer 2f: 0.88 (3H, t, J=6.7, CH$_3$), 1.20-1.35 (18H, m, 9CH$_2$), 1.55-1.61 (2H, m, CH$_2$), 3.35 (3H, s, OCH$_3$), 3.44-3.57 (2H, m, OCH$_2$), 3.60-3.98 (6H, m, CH$^2$+CH$^3$+CH$^4$+CH$^5$+CH$_2^6$), 4.73 (1H, d, J=1.5, CH$^1$); NMR $^{13}$C (75 MHz, CDCl$_3$) $\delta_C$ for the main regioisomer 2f: 14.06 (CH$_3$), 22.63 (CH$_2$), 25.95 (CH$_2$), 29.30 (CH$_2$), 29.42 (CH$_2$), 29.44 (CH$_2$), 29.54 (CH$_2$), 29.57 (CH$_2$), 29.58 (CH$_2$), 29.61 (CH$_2$), 31.86 (CH$_2$), 54.96 (OCH$_3$), 69.50 (CH$^5$), 69.65 (CH$^4$), 70.37 (CH$^2$), 71.12 (CH$_2^6$), 71.67 (CH$_3$), 72.14 (OCH$_2$), 100.7 (CH$^1$); IR $v_{max}$: 3650, 3238 (OH), 2921, 2852, 2159, 2029, 1976, 1156; HRMS (ER$^+$) calculated for C$_{19}$H$_{38}$NaO$_6$: 385.2561 [M+Na]$^+$; measured: 385.2555 (+1.5 ppm); Rf=0.22 (cyclohexane/EtOAc, 60:40).

Example 2g

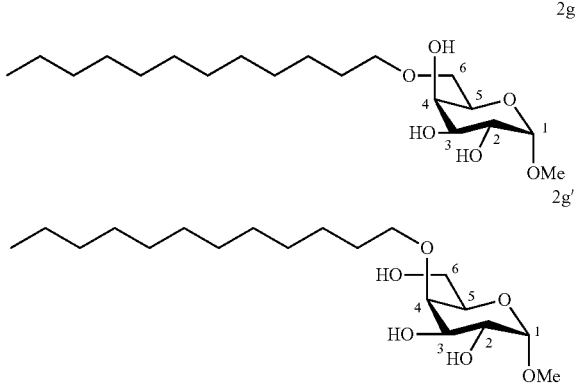

Methyl 6-O-Dodecyl α-D-galactopyranoside (2g) and methyl 4-O-dodecyl α-D-galactopyranoside (2g'):

Compounds 2g and 2g' have been prepared from methyl 4,6-O-dodecylidene α-D-galactopyranoside 1h (0.69 g, 1.90 mmol) following general procedure (B). After reaction, the residue was purified by chromatography on silica gel column (EtOAc/cyclohexane, 50:50). An inseparable 90:10 mixture of 2g and 2g' (0.19 g, 27%) was obtained in the form of a white solid. Melting point=110° C.; NMR $^1$H (300 MHz, CDCl$_3$) $\delta_H$ for the major regioisomer 2g: 0.87 (3H, t, J=6.6, CH$_3$), 1.24 (18H, br s, 9 CH$_2$), 1.55-1.60 (2H, m, CH$_2$), 3.41 (3H, s, OCH$_3$), 3.48 (2H, t, J=6.7, OCH$_2$), 3.67-3.90 (5H, m, 3 CH+CH$_2$), 4.04-4.05 (1H, m, CH), 4.83 (1H, d, J=3.5, CH$_1$); NMR $^{13}$C (75 MHz, CDCl$_3$) $\delta_C$ for the major regioisomer 2g': 14.24 (CH$_3$), 22.81 (CH$_2$), 26.17 (CH$_2$), 29.47 (CH$_2$), 29.59 (CH$_2$), 29.61 (CH$_2$), 29.70 (CH$_2$), 29.74 (CH$_2$), 29.76 (2 CH$_2$), 29.78 (CH$_2$), 32.44 (CH$_2$), 55.59 (OCH$_3$), 69.68 (CH), 70.47 (CH), 71.11 (CH), 71.34 (CH), 72.30 (CH$_2$), 99.84 (CH$^1$); IR $v_{max}$: 3651, 3250 (OH), 2917, 2849, 2493, 2430, 2159, 2029, 1976, 1042; HRMS (ESI$^+$) calculated for C$_{19}$H$_{38}$NaO$_6$: 385.2561 [M+Na]$^+$; measured: 385.2548 (+3.2 ppm); Rf=0.30 (cyclohexane/EtOAc, 40:60).

Example 3: Synthesis of a Sorbitan Ether

Sorbitol Dehydration:
D-sorbitol (20 g, 110 mmol) and 0.1% moles of camphorsulfonic acid are added to a 150-mL stainless-steel autoclave. The reactor is hermetically sealed, purged three times with hydrogen then hydrogen was introduced until the pressure reached 50 bars. The system is then heated to 140° C. and stirred with a mechanical stirrer for 15 hours. After cooling to room temperature, the hydrogen pressure was released and the crude reaction mixture was diluted in ethanol (200 mL) to produce a homogeneous yellow mixture. The solvent is evaporated under low pressure and the residue is then crystallized from cold methanol and filtered under vacuum. The crystalline material was washed with cold methanol to give 1,4-sorbitan (5.88 g, 35% of theory) in the form of a white solid. The purity is >98%, as determined by HPLC, while the crystals had a melting point of 113-114° C. The degree of reaction conversion was determined at 73%, by which a mixture of sorbitol, 1,4-sorbitan, isosorbide and a few by-products in very small quantities were obtained, such that the ratio of 1,4-sorbitan: isosorbide was determined as being 80:20.

Sorbitan Acetalization in DMF:
In a sealed tube, 1,4 sorbitan (0.5 g, 3 mmol) was dissolved in DMF (1.4 mL). Valeraldehyde (107 µL, 1 mmol) was added dropwise under argon followed by the addition of camphorsulfonic acid (10 mg, 10% m) before closing the tube. The mixture is heated to 95° C. with magnetic stirring. After 15 hours, the reaction mixture was cooled and the solvent evaporated under low pressure. A conversion degree of 95% was reached. The residue was diluted in ethyl acetate and the excess 1,4-sorbitan was filtered and washed with ethyl acetate. The filtrate was concentrated under low pressure. The residue was purified by flash chromatography (EtOAc:cyclohexane 80:20 to 100:0) to give the sorbitan acetal (0.22 g, 89% isolated yield) in the form of a colorless oil. HPLC revealed a mixture of 4 isomers.

Trans-Acetalization of Sorbitan in Ethanol:
In a round-bottomed flask 1,4-sorbitan (0.5 g, 3 mmol) was dissolved in ethanol (7.5 mL) and 1,1-diethoxypentane (1.15 mL, 6 mmol) was added under an argon flow, then camphorsulfonic acid (50 mg; 10% w/w). The mixture is heated to 80° C. with magnetic stirring. After 3 hours, the mixture was neutralized and concentrated under low pressure. The residue was purified by flash chromatography (ethyl acetate/cyclohexane 80:20 to 100:0) to give the sorbitan acetal (0.43 g, 66% isolated yield) in the form of a colorless oil. HPLC revealed a mixture of 4 isomers.

Example 4: Synthesis of a Sorbitan Ether

One Pot Synthesis of Sorbitan Ethers from 1,4-sorbitan:
In a 100-mL round-bottomed flask, 1,4-sorbitan (10 g, 62 mmol) is dissolved in dry CPME (30 mL) in the presence of Na$_2$SO$_4$ (6.5 g, 50 mmol), under an argon atmosphere. Valeraldehyde (3.3 mL, 31 mmol) is added, dropwise, followed by Amberlyst 15 (530 mg, 20% m of valeraldehyde). The mixture is heated to 80° C. with magnetic stirring. After 3 hours, the hot mixture is filtered, washed with CPME (2×25 mL) and the filtrate is concentrated under low pressure. Without additional purification, the mixture is diluted in CPME (300 mL), dried on MgSO$_4$ and filtered. The filtrate is put in a 500-mL stainless steel autoclave and 5%-Pd/C (3.3 mg) is added. The reactor is closed well and purged three times with hydrogen before the hydrogen is added under pressure (30 bar). The system is heated at 120° C. and stirred for 15 hours. After having been cooled to ambient temperature, the hydrogen under pressure is released, the reaction mixture is dissolved in absolute ethanol (250 mL) and filtered (0.01 micron Millipore Durapore filter). The filtrate is evaporated under low pressure and the residue (5.8 g) is purified by flash chromatography (EtOAc/cyclohexane 90:10 to 100:0, then EtOH/EtOAc 10:90). In this way a mixture of pentyl-(1,4)-sorbitan ethers (3.97 g, 56%) was obtained in the form of a colorless oil (purity >98% by NMR $^1$H).

Example 5: Measurement of Bacteriostatic Properties of Methyl Glucopyranoside Acetal and Ether Derivatives on Gram-Positive Bacteria The bacteriostatic properties of the derivatives are evaluated by measuring their minimum inhibitory concentration (MIC) on the bacteria tested. These measurements are made using the 96-well microplate microdilution method according to the conditions defined below.

Bacteria Tested:
The minimum inhibitory concentrations (MIC) are tested on Gram-positive bacterial strains according to the recommendations of the "*Clinical Laboratory Standards Institute*" (Clinical-Laboratory-Standards-Institute, 6th ed. Approved standard M100-S17. CLSI, Wayne, Pa., 2007).

The Gram-positive bacteria studied are as follows: *L. monocytogenes* (CIP 103575), *E. faecalis* (ATCC® 29212™) and *S. aureus* (ATCC® 292213™).

The Test Compounds of Interest:
The methyl glucopyranoside C5, C6, C8, C10 and C12 acetals and ethers (number of carbons on the alkyl chain).

Inoculum Preparation:
The cultures studied, freshly isolated (after incubation on a blood agar at 37° C. for 18 h), are taken up in sterile water (10 mL) until obtaining a 0.5 McFarland (Mc) suspension i.e. 1 to 2×10$^8$ CFU (bacteria)/cm$^3$. The bacterial suspension was then diluted to obtain a final concentration of 5×10$^5$ CFU/cm$^3$.

Preparation of Multiwell Plates for Reading the MIC:
Each well contains an identical quantity of Mueller-Hinton medium (a rich medium for bacterial culture) and bacteria with final 5×10$^5$ CFU/cm$^3$.

The test compounds of interest are solubilized in 2.5% m of ethanol before being diluted to different concentrations two by two.

On the multiwell plate, a first series has been planned comprising the culture medium without the test compound of interest. It corresponds to the growth control (control well). These controls serve as reference for comparing bacterial growth with that of the subsequent wells comprising different concentrations of the test compound of interest. The second series of wells comprises the mother solution for the test compound of interest for a concentration in the wells of 4 mM. Each series of wells was diluted two by two until the last series for a final concentration of 0.003 mM. Each concentration is duplicated in the same plate. The plate is incubated for 18 h at 37° C. The reading after incubation shows turbidity in the control wells (revealing bacterial growth). If there is antibacterial activity, the bacterial growth is inhibited, which means that no turbidity or bacterial residue is present. If the test compound inhibits this bacterial growth it may correspond to either bacteriostatic activity in the molecule (inhibits bacterial growth), or to bactericidal activity in the molecule (causes bacteria to die).

Bacterial Count:

To determine whether the agents tested are bactericidal, the minimum bactericidal concentration (MBC) is determined. The MBC corresponds to the concentration leaving a number of bacterial survivors of <4 Log. For this a bacterial count is run from clear wells or without bacterial residue (C≤MIC). To do this, a dilution to 1/100 was conducted with the two wells with the same concentration before seeding on a blood agar using the Spiral technique. After 24 h of incubation at 37° C., the visual count allowed determination of the minimum concentration from which there is no bacterial growth.

Tests on the Methyl Glucopyranoside Acetal and Ether Derivatives

Tests have been conducted on Gram-positive bacteria with methyl glucopyranoside derivatives. The solutions of test compounds are diluted in ethanol at a solvent concentration that does not act on bacterial growth (2.5% m). After sterilization the solutions are diluted in water. The methyl glucopyranoside C10 and C12 acetals have low water solubility. Because precipitates formed in the solutions, the effect of these methyl glucopyranoside C10 and C12 acetals was not able to be evaluated. The results obtained for antimicrobial tests on the 3 bacterial strains *L. monocytogenes* (CIP 103575), *E. faecalis* (ATCC® 29212) and *S. aureus* (ATCC® 292213™) are summarized in Table 1.

The results below (Table 1) reveal that the methyl glucopyranoside derivatives having a hydrophobic chain shorter than 8 carbons (entries 1 and 2) have a minimum inhibitory concentration greater than 4 mM. In other words, these compounds have no inhibiting effect on the growth of Gram-positive bacteria. Inhibition of bacterial growth is observed from compounds having aliphatic chains longer than 8 carbons. Indeed, this is indicated by the absence of turbidity in wells corresponding to the C8 and C10 octylidene methyl glucopyranoside and the mixtures of (4-O-alkyl and 6-O-alkyl) ethers (entries 3 and 4). These compounds present an MIC between 0.12 and 4 mM and more precisely between 2 and 4 mM. Dodecyl methyl glucopyranoside (entry 5) presents the best results. Indeed, an MIC below 0.12 mM and more precisely between 0.12 and 0.03 mM depending on the bacterial strains studied is measured.

TABLE 1

Antimicrobial results for methyl glucopyranoside derivatives on Gram positives: Minimum inhibitory concentration (MIC) in mmol/L

| | | Position | | | | | |
|---|---|---|---|---|---|---|---|
| | | Acetal (Ac) | | | Ether (Eth) | | |
| Entry | Alkyl chain | *L. monocytogenes* | *S. aureus.* | *E. faecalis* | *L. monocytogenes* | *S. aureus.* | *E. faecalis* |
| 1 | C5 | 1a | | | 2a + 2a' 70:30 isomeric mixture in the 6–:4– position | | |
| | | >4 | >4 | >4 | >4 | >4 | >4 |
| 2 | C6 | 1b | | | 2b + 2b' 72:28 isomeric mixture in the 6–:4– position | | |
| | | >4 | >4 | >4 | >4 | >4 | >4 |

TABLE 1-continued

Antimicrobial results for methyl glucopyranoside derivatives on Gram positives: Minimum inhibitory concentration (MIC) in mmol/L

| | | Position | | | | | |
|---|---|---|---|---|---|---|---|
| | | Acetal (Ac) | | | Ether (Eth) | | |
| Entry | Alkyl chain | *L. monocytogenes* | *S. aureus.* | *E. faecalis* | *L. monocytogenes* | *S. aureus.* | *E. faecalis* |
| 3 | C8 | 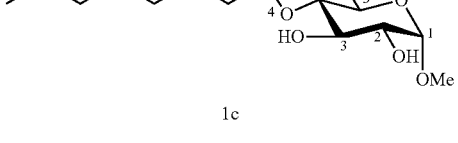<br>1c | | | 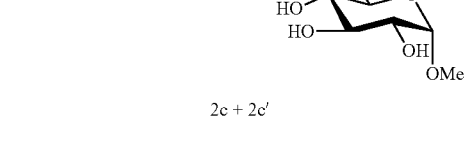<br>2c + 2c'<br>75:25 isomeric mixture in the 6–:4– position | | |
| | | 2 | 4 | 2 | 2 | 2 | 4 |
| 4 | C10 | 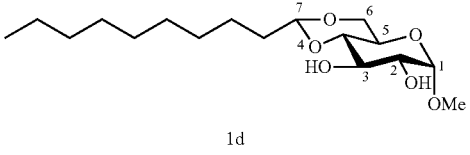<br>1d | | | 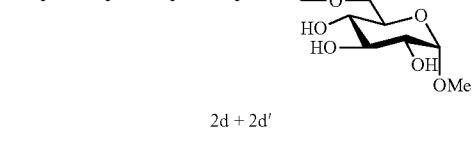<br>2d + 2d'<br>68:32 isomeric mixture in the 6–:4– position | | |
| | | — | — | — | 2 | 0.5 | 2 |
| 5 | C12 | 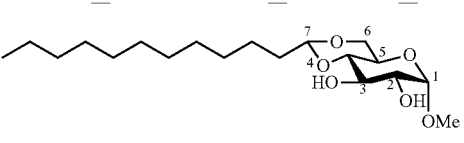<br>1e | | | 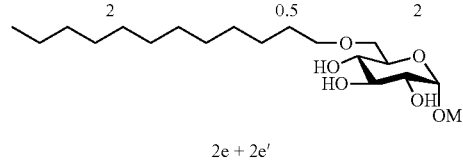<br>2e + 2e'<br>73:27 isomeric mixture in the 6–:4– position | | |
| | | — | — | — | 0.03 | 0.12 | 0.03 |

Example 6: Measurement of Bacteriostatic Properties of Sorbitan Acetal and Ether Derivatives on Gram-Positive Bacteria The sorbitan C5, C6, C8, C10 and C12 acetals and ethers were then tested under the same conditions as previously and on the same bacterial strains (see example 5). The results obtained are given in Table 2.

TABLE 2

Antimicrobial results for sorbitan derivatives on Gram positives: Minimum inhibitory concentration (MIC) in mmol/L

| | | Position | | | | | |
|---|---|---|---|---|---|---|---|
| | | Acetal (Ac) | | | Ether (Eth) | | |
| Entry | Alkyl chain | *L. monocytogenes* | *S. aureus.* | *E. faecalis* | *L. monocytogenes* | *S. aureus.* | *E. faecalis* |
| 1 | C5 | 36:64 isomeric mixture at the (5,6):(3,5) position | | | 33:26:41 isomeric mixture at the 3:5:6 position | | |
| | | >4 | >4 | >4 | >4 | >4 | >4 |

TABLE 2-continued

Antimicrobial results for sorbitan derivatives on Gram positives: Minimum inhibitory concentration (MIC) in mmol/L

| Entry | Alkyl chain | Acetal (Ac) L. monocytogenes | S. aureus. | E. faecalis | Ether (Eth) L. monocytogenes | S. aureus. | E. faecalis |
|---|---|---|---|---|---|---|---|
| 2 | C6 | 57:43 isomeric mixture at the (5,6):(3,5) position >4 | >4 | >4 | 16:33:51 isomeric mixture at the 3:5:6 position >4 | >4 | >4 |
| 3 | C8 | 61:39 isomeric mixture at the (5,6):(3,5) position >4 | >4 | >4 | 22:33:45 isomeric mixture at the 3:5:6 position >4 | >4 | >4 |
| 4 | C10 | 64:36 isomeric mixture at the (5,6):(3,5) position >4 | >4 | >4 | 16:32:52 isomeric mixture at the 3:5:6 position >4 | >4 | >4 |
| 5 | C12 | 50:50 isomeric mixture at the (5,6):(3,5) position 0.03 | 0.12 | 0.03 | 33:27:40 isomeric mixture at the 3:5:6 position 0.12 | 0.12 | 0.12 |

According to observations on the 96-well microplates, the sorbitan ethers and acetals with aliphatic chains less than or equal to 10 carbons do not present antimicrobial properties because all the wells contain turbidity or a bacterial residue. The only bacterial inhibition is observed for compounds derived from dodecyl (entry 5).

Indeed, with concentrations below 12 mM, the sorbitan C12 acetal and ether inhibit the bacterial strains studied. It is noted that the inventors were not able to obtain more soluble C12 compounds that allow analysis of bacteriostatic properties in comparison with the previous methyl glucopyranoside compounds and more particularly 4,6-O-dodecylidene methyl glucopyranoside.

Example 7: Bactericidal Properties of Sorbitan or Methyl Glucopyranoside Acetal and Ether Derivatives on Gram-Positive Bacteria To determine the bactericidal effect of compounds presenting bacteriostatic properties, the wells not presenting any more turbidity from examples 5 and 6 were reseeded on agar. The results obtained after incubation for one night are presented in Table 3.

TABLE 3

Antimicrobial results for methyl glucopyranoside derivatives and sorbitan derivatives on Gram positives: Minimum inhibitory concentration (MIC) in mmol/L, Minimum Bactericidal Concentration (MBC) in mmol/L (in italics)

| | | Methyl glucopyranoside (MeGlu) | | | Sorbitan (Sorb) | |
|---|---|---|---|---|---|---|
| Entry | Bacteria | AcC8 | EthC8 | EthC10 | EthC12 | AcC12 | EthC12 |
| 1 | L. monocytogenes | 2 | 2 | 0.5 | 0.03 | 0.03 | 0.12 |
| 2 | S. aureus | 4 | 2 | 2 | 0.12 | 0.12 | 0.12 |
| 3 | E. faecalis | 4 | 4 | 0.5 | 0.03 | 0.03 | 0.12 |

These results show that the compounds having a C8 group have no bactericidal effect since below 2 to 4 mM, clones are observed on agar after reseeding. Decyl methyl glucopyranoside (EthC10MeGlu,) has an MBC of 0.5 mM for *L. monocytogenes* and *E. faecalis* (entries 1 and 3). Nevertheless, for *S. aureus*, which is a more virulent strain, the MBC rises to 2 mM (entry 2). The strongest bactericidal effect is observed for methyl glucopyranoside C12 ethers (EthC12MeGlu). Indeed, an MBC of 0.12 mM (entry 2) is measured for *S. aureus* and 0.03 mM (entries 1 and 3) for *L. monocytogenes* and *E. faecalis*.

Regarding the sorbitan derivatives, only the compounds containing 12 carbon-chains and presenting bacterial inhibition have been analyzed and compared with the products with the same chain length but on the methyl glucopyranoside. Sorbitan dodecylidene acetal has been revealed to be a bactericidal compound for *L. monocytogenes* and *E. faecalis* strains at 0.03 mM and bacteriostatic for *S. aureus* at 0.12 mM. To confirm that the properties measured on the acetals are indeed those of the amphiphilic compound and not its hydrolysis products, the properties of dodecanal were tested on the different bacterial strains and no antimicrobial activity was observed at concentrations less than or equal to 4 mM. Accordingly, the sorbitan C12 acetal is active as it is and this activity does not come from the corresponding aldehyde.

The mixture of sorbitan dodecyl ethers has an MBC of 0.12 mM for all the Gram-positive strains tested. With MIC of 0.03 mM, the sorbitan acetals are as effective as the methyl glucopyranoside ethers with the same chain length for *L. monocytogenes* and *E. faecalis*. (entries 1 and 3).

However, the mixture of sorbitan C12 ethers is found in the same scale as the EthC12 methyl glucopyranoside for *S. aureus* (entry 2). In addition, sorbitan C12 acetals show the same results as those of the EthC12 methyl glucopyranoside for all of the strains tested. Therefore the conclusion can be drawn that sorbitan C12 acetals and ethers, even in the form of a mixture of regioisomers and diastereoisomers, present very interesting antimicrobial and bactericidal properties.

These results show that sorbitan derivatives may present a new range of biosourced bacteriostatic and bactericidal properties that is very active.

Example 8: Evaluation of Surfactant and Antimicrobial Properties

All of the products synthesized during the study of physical and chemical properties were tested. These analyses show the different profiles from amphiphilic compounds: hydrotropes and surfactants, and the minimum inhibitory concentrations (MIC) values for each compound on Gram-positive bacteria. The best surfactant and antimicrobial results are compared in Table 4.

TABLE 9

Comparison results between the critical micelle concentrations (CMC) and the minimum inhibitory concentrations (MIC) in (mmol/L) on the products of interest: Minimum inhibitory concentration (MIC) in mmol/L

| Entry | Compound | CMC (mM) | MIC (mM) | | |
|---|---|---|---|---|---|
| | | | L. monocytogenes | S. aureus. | E. faecalis |
| 1 | [structure] | 0.012 | 0.03 | 0.12 | 0.03 |
| 2 | [structure] | 0.034 | 0.03 | 0.12 | 0.03 |
| 3 | [structure] | 0.091 | 0.12 | 0.12 | 0.12 |

According to the results above, it is observed that the C12 methyl glucopyranoside and sorbitan derivatives are those that have the best results both for their surfactant and antimicrobial properties (on the Gram-positives) because they present the lowest CMC and MIC. For dodecyl methyl glucopyranoside and dodecylidene sorbitan (entries 1 and 2), the CMC values are within the MIC range. Sorbitan dodecyl ether has a slightly lower CMC (0.09 mM) than its MIC (0.12 mM) but these concentrations are relatively similar all the same (entry 3).

Example 9: Comparison Tests with Compounds Known in the Prior Art

The activity of sorbitan or methyl glucopyranoside derivatives has been compared with that of compounds having similar structures or of a commercial compound like monolaurine (ML) in the table below.

different bacterial strains. Indeed, if the 4-O-EthC12MeGlu was totally inactive, the MIC observed on the (4+6)-O-EthC12MeGlu mixture would necessarily be greater than 0.04 nM.

The connective function between the lipophilic and hydrophilic portions also impacts the MIC values. Accordingly, in the case of dodecyl methyl glucopyranoside derivatives, the MIC are slightly lower for the ethers compared to the corresponding ester (0.03-0.12 mM for EthC12MeGlu and 0.08-0.31 mM for EstC12MeGlu). However, the stability of ether functions in biological medium was higher than the esters (sensitive to esterases), since the compounds comprising an ether function will therefore have prolonged activity over time which makes these derivatives of the compounds particularly advantageous.

TABLE 5

Comparision of results between reference products and methyl glucopyranoside and sorbitan acetals and ethers: Minimum inhibitory concentration (MIC) in mmol/L

| | Compounds known in the prior art | | |
|---|---|---|---|
| Bacteria | ML | 6-EstC12 MeGlu | 6-EthC12 MeGlu pure isomer |
| L. monocytogenes. | 0.04 | 0.08 | 0.04 |
| S. aureus | 0.04 | 0.31 | 0.04 |
| E. faecalis | nd | nd | nd |

| | Compounds tested | | |
|---|---|---|---|
| Bacteria | (4 + 6)-EthC12 MeGlu 73:27 isomeric mixture in the 6– 4– position | EthC12 Sorb 33:27:40 isomeric mixture at the 3:5:6 position | AcC12 Sorb 50:50 isomeric mixture at the 3,5– and 5,6– position |
| L. monocytogenes. | 0.03 | 0.12 | 0.03 |
| S. aureus | 0.12 | 0.12 | 0.12 |
| E. faecalis | 0.03 | 0.12 | 0.03 |

The results obtained demonstrate that the derivatives are as effective as monolaurine (ML) since the difference in MIC obtained between the mixtures of C12 sugar ethers (EthC12MeGlu and EthC12Sorb) and monolaurine is low. What is more, the presence in the form of a mixture of regioisomers of ethers does not affect the antimicrobial properties in light of results between the pure 6-O-EthC12MeGlu (MIC of 0.04 mM on L. monocytogenes) and the (4+6)-O-EthC12MeGlu mixture (MIC of 0.03 mM on L. monocytogenes). This indicates clearly that each of the isomers of the mixture may be active at different degrees on

Example 10: Measurement of Bacteriostatic Properties of Monosaccharide C12 Acetal and Ether Derivatives on Gram-Positive Bacteria Since the best results were observed with compounds having a C12 alkyl group, experiments have been conducted on a wider panel of Gram-positive strains with a mixture of compounds obtained according to the examples 1 and 2.

The Test Compounds of Interest:
Methyl glucopyranoside acetals
Methyl 4,6-O-Dodecylidene α-D-glucopyranoside (1e)

Methyl 4,6-O-Dodecylidene β-D-glucopyranoside (1f)
Mixture of methyl glycopyranoside ethers
Methyl 6-O-Dodecyl α-D-glucopyranoside (2e) and methyl 4-O-dodecyl α-D-glucopyranoside (2e')
Methyl 6-O-Dodecyl α-D-mannopyranoside (2f) and methyl 4-O-dodecyl α-D-mannopyranoside (2f')
Methyl 6-O-Dodecyl α-D-galactopyranoside (2g) and methyl 4-O-dodecyl α-D-galactopyranoside (2g')
Mixtures of sorbitan ethers
3-O-Dodecyl-1,4-D-sorbitan, 5-O-dodecyl-1,4-D-sorbitan and 6-O-dodecyl-1,4-D-sorbitan Inoculum Preparation:

The cultures studied, freshly isolated (after incubation on a blood agar at 37° C. for 18 h), are taken up in sterile water (10 mL) until obtaining a 0.5 McFarland (Mc) suspension i.e. 1 to 1 to 2×10$^8$ CFU (bacteria)/cm$^3$. The bacterial suspension was then diluted to obtain a final concentration of 1×10$^6$ CFU/cm$^3$.

Preparation of Multiwell Plates for Reading the MIC:

Each well contains an identical quantity of Mueller-Hinton medium (a rich medium for bacterial culture) and bacteria with final [concentration of] 0.5×10$^6$ CFU/cm$^3$.

The test compounds of interest are solubilized in ethanol or DMSO at 25 mg/mL before being diluted to different concentrations two by two. On the multiwell plate, a first series has been planned comprising the culture medium without the test compound of interest. It corresponds to the growth control (control well). These controls serve as reference for comparing bacterial growth with that of the subsequent wells comprising different concentrations of the test compound of interest. The second series of wells comprises the mother solution for the test compound of interest for a concentration in the wells of 256 mg/L (7 mM). Each series of wells was diluted two by two until the last series for a final concentration of 0.25 mg/L (0.0007 mM). Each concentration is duplicated in the same plate. The plate is incubated for 18 h at 37° C. The reading after incubation shows turbidity in the control wells (revealing bacterial growth). If there is antibacterial activity, the bacterial growth is inhibited, which means that no turbidity or bacterial residue is present.

The minimum inhibitory concentrations (MIC) are tested on Gram-positive bacterial strains according to the recommendations of the "Clinical Laboratory Standards Institute" (Clinical-Laboratory-Standards-Institute, 6th ed. Approved standard M100-S17. CLSI, Wayne, Pa., 2007). The clinical strains have been isolated in the Hospice de Lyon.

The Gram-positive bacteria studied are as follows:
Staphylococci *S. aureus*: ATCC® 29213™, ATCC 25923,
*Staphylococci* strains Methicillin-resistant *S. aureus* (Lac-Deleo USA 300), (MU 3), (HT 2004-0012), LY 199-0053, (HT 2002-0417), (HT 2006-1004),
*Staphylococci* strains Daptomycin-resistant *S. aureus* (ST 2015-0188), (ST 2014 1288), (ST 2015-0989).
*Enterococci*: *E. faecalis* (ATCC® 29212™), clinical enterococci strains *E. faecalis* isolated from urines: strain 015206179901 (hereinafter 9901), strain 015205261801 (hereinafter 1801)
*Enterococci*: *E. faecium* (CIP 103510), clinical strains of *Enterococci E. faecium*: Van A 0151850763 (hereinafter Van A); strain 015 205731401 (hereinafter 1401),
*Listeria*: *L. monocytogenes* (CIP 103575), clinical strain isolated from hemoculture (015189074801, LM1), a strain isolated from cerebrospinal liquid (015170199001, LM2), clinical strains isolated from hemoculture (015181840701, LM3).

Inoculum Preparation:

The cultures studied, freshly isolated (after incubation on a blood agar at 37° C. for 18 h), are taken up in sterile water (10 mL) until obtaining a 0.5 McFarland (Mc) suspension i.e. At 10$^8$ CFU (bacteria)/cm$^3$. The bacterial suspension was then diluted to obtain a final concentration of 10$^6$ CFU/cm$^3$.

Results for the Strains of Genus *Staphylococcus*

TABLE 6

Antimicrobial results from the methyl glycopyranoside and sorbitan ether and acetal derivatives on different strains of *Staphylococcus S Aureus*: Minimum inhibitory concentration (MIC) in mg/L

| | | | | | Staphylococcus | | | | | | |
|---|---|---|---|---|---|---|---|---|---|---|---|
| ATCC 25923 | ATCC 29213 | USA 300 | MU 3 | HT 2004-0012 | LY 199-0053 | HT 2002-0417 | HT 2006-1004 | ST 2015-0188 | ST 2014 1288 | ST 2015 0989 |
| C12-Ac-α-MeGlu 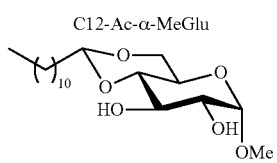 1e | 256 | 256 | 256 | 256 | 256 | 256 | 256 | 256 | / | / | / |
| C12-Ac-β-MeGlu 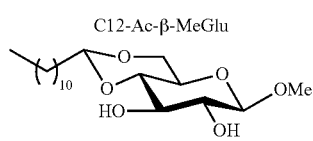 1f | 64 | 64 | 64 | 64 | | 64 | 128 | 64 | 64 | 64 | 64 |

TABLE 6-continued

Antimicrobial results from the methyl glycopyranoside and sorbitan ether and acetal derivatives on different strains of *Staphylococcus S Aureus*: Minimum inhibitory concentration (MIC) in mg/L

| | Staphylococcus | | | | | | | | | | |
|---|---|---|---|---|---|---|---|---|---|---|---|
| | ATCC 25923 | ATCC 29213 | USA 300 | MU 3 | HT 2004-0012 | LY 199-0053 | HT 2002-0417 | HT 2006-1004 | ST 2015 0188 | ST 2014 1288 | ST 2015 0989 |
| C12-Eth-α-MeGlu  2e + 2e′ | 16 | 32 | 32 | 32 | 32 | 16 | 16 | 32 | 32 | 32 | 32 |
| C12-Eth-α-MeMan  2f + 2f′ | 32 | 32 | 32 | 64 | 32 | 32 | 32 | 64 | 64 | 32 | 64 |
| C12-Eth-α-MeGalac  2g + 2g′ | 124 | 256 | 256 | 256 | 128 | 246 | 256 | 256 | 256 | 256 | 256 |
| C12-Eth-Sorb | 32 | 32 | 32 | 64 | 32 | 32 | 32 | 32 | 64 | 64 | 256 |

According to observations on the 96-well microplates, any of the acetal or ether monosaccharide derivatives are active against the *staphylococcus* strains tested (8<MIC<64 mg/L) with the exception of the galactose ether (C12-Eth-α-MeGalac) and the glucose α-acetal (C12-Ac-α-MeGlu) (MIC>256 mg/L).

Results for the Strains of Genus *Enterococcus*

TABLE 7

Antimicrobial results for sugar ether and sugar acetal and sorbitan derivatives on different *enterococcus* strains. Minimum inhibitory concentration (MIC) in mg/L

| | Enterococcus | | | | | |
|---|---|---|---|---|---|---|
| | ATCC 29212 | Van A | CIP 103510 | 1401 | 9901 | 1801 |
| C12-Ac-α-MeGlu  1e | 256 | 256 | 256 | / | / | / |

TABLE 7-continued

*Antimicrobial results for sugar ether and sugar acetal and sorbitan derivatives on different enterococcus strains. Minimum inhibitory concentration (MIC) in mg/L*

| | | Enterococcus | | | | |
|---|---|---|---|---|---|---|
| | ATCC 29212 | Van A | CIP 103510 | 1401 | 9901 | 1801 |
| C12-Ac-β-MeGlu (1f) | 64 | 32 | 32 | 16 | 32 | 8 |
| C12-Eth-α-MeGlu (2e + 2e') | 16 | 16 | 16 | 8 | 16 | 8 |
| C12-Eth-α-MeMan (2f + 2f') | 16 | 16 | 32 | 16 | 32 | 16 |
| C12-Eth-α-MeGalac (2g + 2g') | 64 | 124 | 256 | 32 | 64 | 8 |
| C12-Eth-Sorb | 8 | 16 | 16 | 8 | 16 | 8 |

Good antibacterial activity observed for all the *enterococcus* strains 32<MIC<8 mg/L for all the molecules tested with the exception of the α-glucose acetal (C12-Ac-α-MeGlu).

Results for Strains of the *Listeria* Genus

TABLE 8

Antimicrobial results for sugar ether derivatives and sugar and sorbitan acetals on different strains of *Listeria* Minimum inhibitory concentration (MIC) in mg/L.

| | *Listeria* | | | |
|---|---|---|---|---|
| | CIP 103575 | LM1 | LM2 | LM3 |
| C12-Ac-α-MeGlu (1e) | 64 | / | / | / |
| C12-Ac-β-MeGlu (1f) | 16 | 16 | 16 | 64 |
| C12-Eth-α-MeGlu (2e + 2e') | 8 | 8 | 8 | 8 |
| C12-Eth-α-MeMan (2f + 2f') | 32 | 8 | 16 | 16 |
| C12-Eth-α-MeGalac (2g + 2g') | 64 | 64 | 64 | 64 |
| C12-Eth-Sorb | 32 | 16 | 32 | 32 |

Good antibacterial activity observed on all the *Listeria* strains 64<MIC<8 mg/L for all the molecules tested.

The invention claimed is:

1. A method for disinfection or prevention of bacterial colonization by Gram-positive bacteria of a substrate, comprising:
putting a substrate into contact with a composition comprising a mixture of positional isomers of alkyl monoethers or monoacetals of monosaccharides or monosaccharide alkylglycosides or pharmaceutically acceptable salts thereof, said alkyl group comprising between 11 to 18 carbon atoms, and said alkyl monoethers or monoacetals presenting an ether alkyl or acetal alkyl group on two distinct positions of the monosaccharide or monosaccharide alkylglycoside.

2. The method as claimed in claim 1, wherein the mixture of positional isomers of alkyl monoethers or monoacetals of monosaccharides or monosaccharide alkylglycosides is obtained by a process comprising the following steps:
a) an acetalization or trans-acetalization of a monosaccharide or monosaccharide alkylglycoside by an aliphatic aldehyde containing from 11 to 18 carbon atoms or the acetal thereof, and
b) recovery of a mixture of alkyl monoether positional isomers of monosaccharide or monosaccharide alkylglycosides obtained by catalytic hydrogenolysis of the alkyl acetal monosaccharide or monosaccharide alkylglycoside obtained in a), in which the alkyl group (R) comprises between 11 to 18 carbon atoms,
or
recovery of a mixture of monosaccharide or monosaccharide derivative alkyl monoacetal positional isomers obtained in a) in which the alkyl group (R) comprises between 11 to 18 carbon atoms.

3. The method as claimed in claim 1, wherein the monosaccharide is a C6 monosaccharide or an alkylglycoside thereof.

4. The method as claimed in claim 1, wherein the monosaccharide is a glucoside and said alkyl monoacetal group is in the 1,2-O—, 2,3-O—, 3,4-O— or -4,6-O— position or said alkyl monoether group is in the 4-O— or 6-O— position.

5. The method as claimed in claim 1, wherein the Gram-positive bacteria are bacteria from the phylum of Firmicutes.

6. The method as claimed in claim 1, wherein the Gram-positive bacteria are bacteria of the order of Bacillales chosen from the family of Alicyclobacillaceae, Bacillaceae, Caryophanaceae, Listeriaceae, Paenibacillceae, Pasteuriaceae, Planococcaceae, Sporolactobacillaceae, Slaphylococcaceae, Thermoactinomycelacea and Turicibacteraceae.

7. The method as claimed in claim 1, wherein the Gram-positive bacteria are bacteria from the family of Listeriaceae chosen from *L. fleischmannii*, *L. grayi*, *L. innocua*, *L. ivanovii*, *L. marthii*, *L. monocytogenes*, *L. rocourtiae*, *L. seeligeri*, *L. weihenstephanensis* and *L. welshimeri*.

8. The method as claimed in claim 1, wherein the Gram-positive bacteria are bacteria from the family of Staphylococcaceae chosen from bacteria from the genus *Staphylococcus*, *Gemella*, *Jeotgalicoccus*, *Macrococcus*, *Salinicoccus* and *Nosocomiicoccu*.

9. The method as claimed in claim 1, wherein the Gram-positive bacteria are bacteria from the genus *Staphylococcus* chosen from chosen from *S. arlettae*, *S. agnetis*, *S. aureus*, *S. auricularis*, *S. capitis*, *S. caprae*, *S. carnosus*, *S. caseolyticus*, *S. chromogenes*, *S. cohnii*, *S. condimenti*, *S. delphini*, *S. devriesei*, *S. epidermidis*, *S. equorum*, *S. felis*, *S. fleurettii*, *S. gallinarum*, *S. haemolyticus*, *S. hominis*, *S. hyicus*, *S. inter-*

*medius, S. kloosii, S. leei, S. lentus, S. lugdunensis, S. lutrae, S. massiliensis, S. microti, S. muscae, S. nepalensis, S. pasteuri, S. pettenkoferi, S. piscifermentans, S. pseudintermedius, S. pseudolugdunensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri* and *S. xylosus*.

10. The method as claimed in claim 1, wherein the Gram-positive bacteria are Lactobacillales chosen from a family of Aerococcaceae, Carnobacteriaceae, Enterococcaceae, Lactobacillaceae, Leuconostocaceae and Streptococcaceae.

11. The method as claimed in claim 1, wherein the Gram-positive bacteria are bacteria from the family of Enterococcaceae chosen from bacteria in the genus *Bavariicoccus, Catellicoccus, Enterococcus, Melissococcus, Pilibacter, Tetragenococcus, Vagococcus*.

12. The method as claimed in claim 1, wherein the Gram-positive bacteria are bacteria from the *Enterococcus* genus chosen from *E. malodoratus, E. avium, E. durans, E. faecalis, E. faecium, E. gallinarum, E. hirae, E. solitarius*, preferentially, *E. avium, E. durans, E. faecalis* and *E. faecium*.

13. The method as claimed in claim 1, wherein the substrate is a food, cosmetic, pharmaceutical, phytosanitary, veterinary composition or surface.

14. The method as claimed in claim 1, wherein the method is used externally for a dermatological purpose.

15. The method as claimed in claim 14, wherein the infection by Gram-positive bacteria is an infection of the skin or mucous membranes.

16. The method as claimed in claim 2, wherein the process further comprises the catalytic hydrogenolysis of the obtained alkyl monosaccharide or monosaccharide alklylglycoside acetal.

17. The method as claimed in claim 16, wherein the catalytic hydrogenolysis is performed without an acid catalyst.

18. The method as claimed in claim 1, wherein the alkyl group comprises from 11 to 13 carbon atoms.

19. The method as claimed in claim 1, wherein the monosaccharide is:
a hexose chosen from the group formed by glucose, mannose, galactose, allose, altrose, gulose, idose and talose.

20. The method as claimed in claim 15, wherein the infection is an infection chosen from folliculitis, abscesses, paronychia, boils, impetigo, infections between the digits, anthrax (staphylococcal anthrax), cellulitis, secondary wound infections, otitis, sinusitis, hidradenitis, infectious mastitis, post-traumatic skin infections or infections on burnt skin.

* * * * *